US010590171B2

(12) United States Patent
Silvas et al.

(10) Patent No.: US 10,590,171 B2
(45) Date of Patent: Mar. 17, 2020

(54) EXOSOMES AND METHODS OF MAKING AND USING THE SAME

(71) Applicants: Jesus A. Silvas, Fayetteville, GA (US); Patricia V. Aguilar, Galveston, TX (US); Vsevolod L. Popov, Galveston, TX (US)

(72) Inventors: Jesus A. Silvas, Fayetteville, GA (US); Patricia V. Aguilar, Galveston, TX (US); Vsevolod L. Popov, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/795,729

(22) Filed: Oct. 27, 2017

(65) Prior Publication Data

US 2018/0134754 A1 May 17, 2018

Related U.S. Application Data

(60) Provisional application No. 62/414,416, filed on Oct. 28, 2016.

(51) Int. Cl.
*C07K 14/005* (2006.01)
*C07K 14/705* (2006.01)
*C12N 7/00* (2006.01)
*A61K 47/42* (2017.01)

(52) U.S. Cl.
CPC ............ *C07K 14/005* (2013.01); *A61K 47/42* (2013.01); *C07K 14/70596* (2013.01); *C12N 7/00* (2013.01); *C12N 2740/16043* (2013.01); *C12N 2760/12221* (2013.01); *C12N 2760/12222* (2013.01)

(58) Field of Classification Search
None
See application file for complete search history.

(56) References Cited

U.S. PATENT DOCUMENTS

| | | | | |
|---|---|---|---|---|
| 8,252,574 | B2 | 8/2012 | Mason et al. | |
| 9,085,778 | B2 | 7/2015 | Lötvall et al. | |
| 9,109,199 | B2 | 8/2015 | Kortekaas et al. | |
| 9,347,087 | B2 | 5/2016 | Vlassov et al. | |
| 9,421,250 | B2 | 8/2016 | McMullan et al. | |
| 2010/0047277 | A1 | 2/2010 | Compans et al. | |
| 2018/0134754 | A1* | 5/2018 | Silvas .................. | C07K 14/005 |

OTHER PUBLICATIONS alignment if SEQ ID No. 1 with UniProt F1BA49_9VIRU Yu May 2011.* alignment of instant SEQ ID No. 2 with UniProt F1BA47_9VIRU Yu May 2011.*

Abstract for Grant No. 1R21AI115286-01A1, awarded Jun. 12, 2015 by the National Institutes of Health. "Hijacking of cellular pathways by novel tick-borne phlebovirus."

Bao et al., "A family cluster of infections by a newly recognized bunyavirus in eastern China, 2007: further evidence of person-to-person transmission," *Clin Infect Dis*, 2011; 53:1208-1214.

Bird et al., "Nonlytic viral spread enhanced by autophagy components," *Proc Natl Acad Sci U S A*, 2014; 111:13081-13086.

Blakqori et al., "La Crosse bunyavirus nonstructural protein NSs serves to suppress the type I interferon system of mammalian hosts," *J Virol*, 2007; 81:4991-4999.

Brennan et al., "Reverse genetics system for severe fever with thrombocytopenia syndrome virus," *J Virol*, 2015; 89:3026-3037.

Bridgen et al., "Bunyamwera bunyavirus nonstructural protein NSs is a nonessential gene product that contributes to viral pathogenesis," *Proc Natl Acad Sci U S A*, 2001; 98:664-669.

Bukong et al., "Exosomes from hepatitis C infected patients transmit HCV infection and contain replication competent viral RNA in complex with Ago2-miR122-HSP90," *PLoS Pathog*, 2014; 10:e1004424.

Chang and Woo, "Severe Fever with thrombocytopenia syndrome: tick-mediated viral disease," *J Korean Med Sci*, 2013; 28:795-796.

Chaput et al., "Exosomes: immune properties and potential clinical implementations," *Semin Immunopathol*, 2011; 33(5):419-440.

Colombo et al., "Biogenesis, secretion, and intercellular interactions of exosomes and other extracellular vesicles," *Annu Rev Cell Dev Biol*, 2014; 30:255-289.

Ding et al., "Epidemiologic features of severe fever with thrombocytopenia syndrome in China, 2011-2012," *Clin Infect Dis*, 2013; 56:1682-1683.

Edgar, "Q&A: What are exosomes, exactly?" *BMC Biology*, 2016; 14:46.

Elliott and Weber, "Bunyaviruses and the type I interferon system," *Viruses*, 2009; 1:1003-1021.

Escola et al., "Selective enrichment of tetraspan proteins on the internal vesicles of multivesicular endosomes and on exosomes secreted by human B-lymphocytes," *J Biol Chem*, 1998; 273:20121-20127.

Feng et al., "A pathogenic picornavirus acquires an envelope by hijacking cellular membranes," *Nature*, 2013; 496:367-371.

Ferguson et al., "Exosomes as therapeutics: the implications of molecular composition and exosomal heterogeneity," *J Control Release*, 2016; 228:179-190.

Fontana et al., "The unique architecture of Bunyamwera virus factories around the Golgi complex," *Cell Microbiol*, 2008; 10:2012-2028.

Guu et al., "Bunyavirus: structure and replication," *Adv Exp Med Biol*, 2012; 726:245-266.

Harding et al., "Endocytosis and intracellular processing of transferrin and colloidal gold-transferrin in rat reticulocytes: demonstration of a pathway for receptor shedding," *Eur J Cell Biol*, 1984; 35:256-263.

Hartman et al., "Increasing vaccine potency through exosome antigen targeting," *Vaccine*, 2011; 29(50):9361-9367.

(Continued)

*Primary Examiner* — Shanon A. Foley
(74) *Attorney, Agent, or Firm* — Mueting, Raasch & Gebhardt, P.A.

(57) ABSTRACT

Provided herein are isolated exosomes. An exome can include a nonstructural (NSs) protein of a virus, a glycoprotein (Gn protein) of a virus, or a combination thereof. The virus is a member of the Order Bunyavirales, such as a member of the genus *Phlebovirus*. In one embodiment, the virus is Severe Fever with Thrombocytopenia Syndrome (SFTS) virus. Also provided are methods for making and using the exosomes described herein.

13 Claims, 14 Drawing Sheets

Specification includes a Sequence Listing.

(56) References Cited

OTHER PUBLICATIONS

Huang et al., "Enterovirus 71-induced autophagy detected in vitro and in vivo promotes viral replication," *J Med Virol*, 2009; 81:1241-1252.
Ichimura et al., "A ubiquitin-like system mediates protein lipidation," *Nature*, 2000; 408:488-492.
Jiao et al., "Preparation and evaluation of recombinant severe fever with thrombocytopenia syndrome virus nucleocapsid protein for detection of total antibodies in human and animal sera by double-antigen sandwich enzyme-linked immunosorbent assay," *J Clin Microbiol*, 2012; 50:372-377.
Kabeya et al., "LC3, a mammalian homologue of yeast Apg8p, is localized in autophagosome membranes after processing," *EMBO J*, 2000; 19:5720-5728.
Kalamvoki et al., "Cells infected with herpes simplex virus 1 export to uninfected cells exosomes containing STING, viral mRNAs, and microRNAs," *Proc Natl Acad Sci U S A*, 2014; 111:E4991-E4996.
Kim et al., "Severe fever with thrombocytopenia syndrome, South Korea, 2012," *Emerg Infect Dis*, 2013; 19:1892-1894.
Klein and Jackson, "Human rhinovirus 2 induces the autophagic pathway and replicates more efficiently in autophagic cells," *J Virol*, 2011; 85:9651-9654.
Komatsu et al., "Impairment of starvation-induced and constitutive autophagy in Atg7-deficient mice," *J Cell Biol*, 2005; 169:425-434.
Lai et al., "Microvesicles: ubiquitous contributors to infection and immunity," *J Leukoc Biol*, 2015; 97:237-245.
Lattanzi et al., "A strategy of antigen incorportaion into exosomes: comparing cross-presentation levels of antigens delivered by engineered exosomes and by lentiviral virus-like particles," *Vaccine*, 2012; 30(50):7229-7237.
Liu et al., "Person-to-person transmission of severe fever with thrombocytopenia syndrome virus," *Vector Borne Zoonotic Dis*, 2012; 12:156-160.
Liu et al., "Severe fever with thrombocytopenia syndrome, an emerging tick-borne zoonosis," *Lancet Infect Dis*, 2014; 14:763-772.
Lozach et al., "Entry of bunyaviruses into mammalian cells," *Cell Host Microbe*, 2010; 7:488-499.
Mack et al., "Transfer of the chemokine receptor CCR5 between cells by membrane-derived microparticles: a mechanism for cellular human immunodeficiency virus 1 infection," *Nat Med*, 2000; 6:769-775.
McMullan et al., "A new phlebovirus associated with severe febrile illness in Missouri," *N Engl J Med*, 2012; 367:834-841.
Muehlenbachs et al., "Heartland virus-associated death in Tennessee," *Clin Infect Dis*, 2014; 59:845-850.
Natasha et al., "Exosomes as immunotheranostic nanoparticles," *Clin Ther*, 2014; 36(6):820-829.
National Center for Biotechnology Information, National Library of Medicine, National Institutes of Health, GenBank Locus NC_018137, Accession No. NC_018137, "SFTS virus HB29 segment S, complete genome," [online]. Bethesda, MD [retrieved on Mar. 21, 2018]. Retrieved from the Internet: <URL:https://www.ncbi.nlm.nih.gov/nuccore/NC_018137.1>; 2 pgs.
Ning et al., "Viral suppression of innate immunity via spatial isolation of TBK1/IKKε from mitochondrial antiviral platform," *J Mol Cell Biol*, 2014; 6:324-337.
Ning et al., "Disruption of type I interferon signaling by the nonstructural protein of severe fever with thrombocytopenia syndrome virus via the hijacking of STAT2 and STAT1 into inclusion bodies," *J Virol*, 2015; 89:4227-4236.
Novoa et al., "Key Golgi factors for structural and functional maturation of bunyamwera virus," *J Virol*, 2005; 79:10852-10863.
O'Donnell et al., "Foot-and-mouth disease virus utilizes an autophagic pathway during viral replication," *Virology*, 2011; 410:142-150.
Palacios et al., "Characterization of the Uukuniemi virus group (Phlebovirus: Bunyaviridae): evidence for seven distinct species," *J Virol*, 2013; 87:3187-3195.
Pan et al., "Electron microscopic evidence for externalization of the transferrin receptor in vesicular form in sheep reticulocytes," *J Cell Biol*, 1985; 101:942-948.
Pegtel et al., "Functional delivery of viral miRNAs via exosomes," *Proc Natl Acad Sci U S A*, 2010; 107:6328-6333.
Ramakrishnaiah et al., "Exosome-mediated transmission of hepatitis C virus between human hepatoma Huh7.5 cells," *Proc Natl Acad Sci U S A*, 2013; 110:13109-13113.
Raposo et al., "B lymphocytes secrete antigen-presenting vesicles," *J Exp Med*, 1996; 183:1161-1172.
Raposo and Stoorvogel, "Extracellular vesicles: exosomes, microvesicles, and friends," *J Cell Biol*, 2013; 200:373-383.
Reggiori et al., "Coronaviruses hijack the LC3-I-positive EDEMosomes, ER-derived vesicles exporting short-lived ERAD regulators, for replication," *Cell Host Microbe*, 2010; 7:500-508.
Reggiori et al., "Unconventional use of LC3 by coronaviruses through the alleged subversion of the ERAD tuning pathway," *Viruses*, 2011; 3:1610-1623.
Robinson et al., "Coxsackievirus B exits the host cell in shed microvesicles displaying autophagosomal markers," *PLoS Pathog*, 2014; 10:e1004045.
Salanueva et al., "Polymorphism and structural maturation of bunyamwera virus in Golgi and post-Golgi compartments," *J Virol*, 2003; 77:1368-1381.
Sambrook et al. (Eds.), *Molecular Cloning: A Laboratory Manual*, Cold Spring Harbor Laboratory Press: Cold Spring Harbor, NY; 1989. Title page, publisher's page, and table of contents; 30 pgs.
Santiago et al., "Hijacking of RIG-I signaling proteins into virus-induced cytoplasmic structures correlates with the inhibition of type I interferon responses," *J Virol*, 2014; 88:4572-4585.
Silvas et al., "Extracelluar vesicles mediate receptor-independent transmission of novel tick-borne bunyavirus," *Journal of Virology*, 2016; 90(2):873-886.
Tatusova et al., "BLAST 2 Sequences, a new tool for comparing protein and nucleotide sequences," *FEMS Microbiol Lett.*, May 1999; 174(2):247-250.
Valadi et al., "Exosome-mediated transfer of mRNAs and microRNAs is a novel mechanism of genetic exchange between cells," *Nat Cell Biol*, 2007; 9:654-659.
Vallhov et al., "Exosomes containing glycoprotein 350 released by EBV-transformed B cells selectively target B cells through CD21 and block EBV infection in vitro," *J Immunol*, 2011; 186(1):73-82.
Wang et al., "Novel phlebovirus with zoonotic potential isolated from ticks, Australia," *Emerg Infect Dis*, 2014; 20:1040-1043.
Wang et al., "Person-to-person asymptomatic infection of severe fever with thrombocytopenia syndrome virus through blood contact," *Internal Medicine*, 2014; 53:903-906.
Wu et al., "Roles of viroplasm-like structures formed by nonstructural protein NSs in infection with severe fever with thrombocytopenia syndrome virus," *FASEB J*, 2014; 28:2504-2516.9.
Wu et al., "Evasion of antiviral immunity through sequestering of TBK1/IKKε/IRF3 into viral inclusion bodies," *J Virol*, 2014; 88:3067-3076.
Yu et al., "Fever with thrombocytopenia associated with a novel bunyavirus in China," *N Engl J Med*, 2011; 364:1523-1532.
Yun et al., "Severe fever with thrombocytopenia syndrome virus in ticks collected from humans, South Korea, 2013," *Emerg Infect Dis*, 2014; 20:1358-1361.
Zeelenberg et al., "Targeting tumor antigens to secreted membrane vesicles in vivo induces efficient antitumor immune responses," *Cancer Res*, 2008; 68(4):1228-1235.
Zhang et al., "An emerging hemorrhagic fever in China caused by a novel bunyavirus SFTSV," *Sci China Life Sci*, 2013; 56:697-700.

* cited by examiner

Fig. 1A
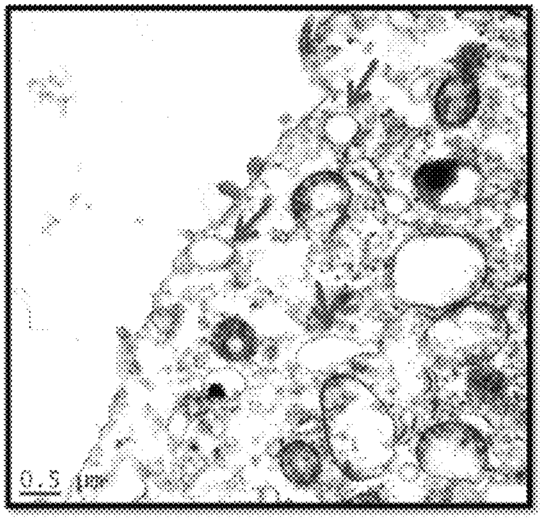
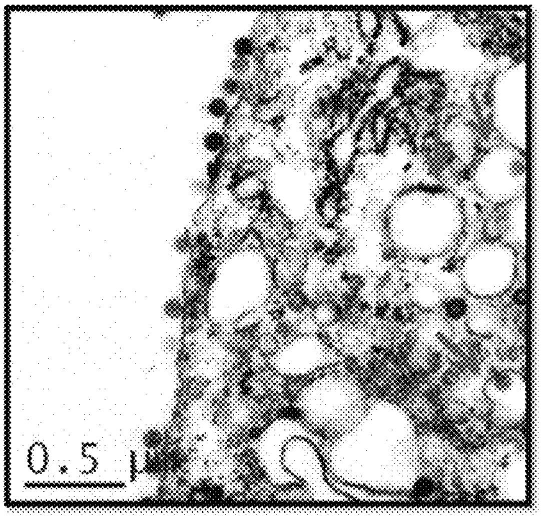
Fig. 1B
Fig. 1C
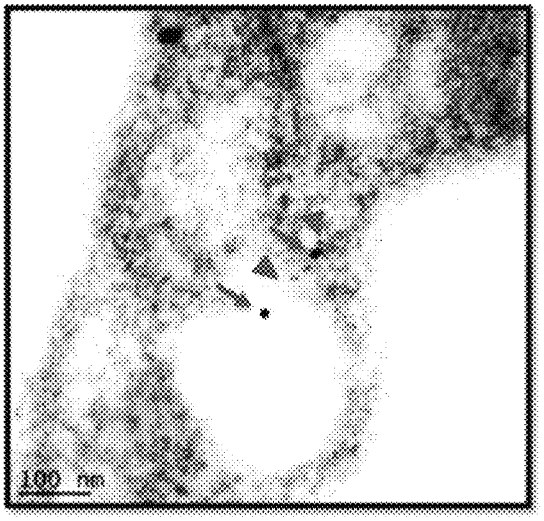
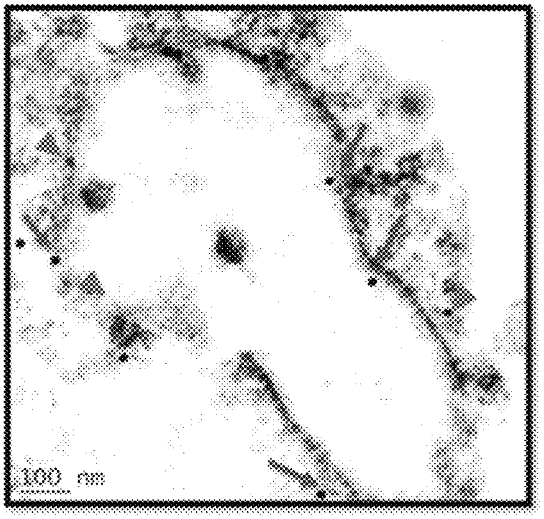
Fig. 1D

SFTS virus NSs-mCherry / mcherry

Negative Stain

Immuno-gold

SFTS virus NSs (1.5nm) →
CD63 (6nm) →

50nm

Mock / SFTS virus

Negative Stain

Immuno-gold

SFTS virus NSs (1.5nm) →
CD63 (6nm) →

50nm

EXOSOMES AND METHODS OF MAKING AND USING THE SAME

CROSS-REFERENCE TO RELATED APPLICATIONS

This application claims the benefit of U.S. Provisional Application Ser. No. 62/414,416, filed Oct. 28, 2016, which is incorporated by reference herein.

GOVERNMENT FUNDING

This invention was made with government support under 1R21AI115286-01A1, awarded by the National Institutes of Health. The government has certain rights in the invention.

SEQUENCE LISTING

This application contains a Sequence Listing electronically submitted via EFS-Web to the United States Patent and Trademark Office as an ASCII text file entitled "265-00930101-Seq-Listing_ST25.txt" having a size of 8 kilobytes and created on Jan. 24, 2018. The information contained in the Sequence Listing is incorporated by reference herein.

BACKGROUND

The Bunyavirales order includes five genera, including *Orthobunyavirus, Phlebovirus, Nairovirus, Hantavirus*, and *Tospovirus*. The majority of viruses within this order (with the exception of Hantaviruses) are considered arthropod-borne viruses and are important causes of morbidity and mortality around the world. These viruses are associated with a range of clinical symptoms characterized by febrile illness and in the most severe cases fatal hepatitis, hemorrhagic fever, or neurological manifestations requiring intensive care have been reported.

Due to advances in genomic and virus identification approaches, novel bunyaviruses have been discovered and identified as important causes of human disease during recent years (1-3). One example is severe fever with thrombocytopenia syndrome (SFTS) virus, a new member of the order Bunyavirales, genus *Phlebovirus* (1, 4). The virus was first isolated in China in 2009 from patients presenting with a hemorrhagic fever illness (1, 5). The initial case fatality rate reported for SFTS was 12 to 30%, and a recent serosurvey among persons living in rural Jiangsu Province found that 3.6% of residents had neutralizing antibodies to SFTS virus (6). Evidence has also been obtained about the possibility of person-to-person transmission (7, 8). Furthermore, hemorrhagic fever cases with mortality rates as high as 50% have now been recognized in Japan and Korea, further highlighting the emerging potential of this pathogen (1, 2, 9-11). Therefore, SFTS virus is a highly pathogenic phlebovirus, and due to its recent emergence, the mechanism of disease pathogenesis is still unclear.

Like other members of the order Bunyavirales, SFTS virus possesses a negative sense tripartite genome consisting of the S, M, and L segments. The L segment encodes the viral RNA polymerase (L), the M segment encodes glycoproteins (Gn/Gc), and the S segment uses an ambisense coding strategy to encode a nonstructural protein (NSs) and a nucleocapsid protein (NP) (12). Although many bunyaviruses, including the prototype virus in the Bunyavirales order Bunyamwera virus (BUNV), also encodes the nonstructural protein NSm within the M segment, some members of the *Phlebovirus* genus, including SFTS and Uukuniemi viruses (UUKV) do not encode this viral protein (1, 13). The BUNV NSm is known to serve as a scaffold protein that associates to globular and tubular structures derived from the Golgi apparatus (14-16). These structures have been shown to harbor the ribonucleoprotein (RNP), a complex essential for the transcription and replication of viral RNA (14). Although SFTS virus does not encode the NSm protein, it has been recently suggested that the SFTS virus NSs may exert some of the NSm's function by serving as a scaffold protein and forming viral replication factories (17). Colocalization of the early endosomal marker Rab5 with the viral factories induced by SFTS virus NSs suggests that these structures are of endosomal origin and not derived from the Golgi apparatus (18). Additionally, the SFTS virus NSs protein has also been shown to play a role in the inhibition of host innate immunity (18, 19). Although these findings are consistent with previous studies on bunyavirus NSs proteins describing the NSs as a major virulence factor that acts as a global inhibitor of host cell transcription and antagonist of the IFN system (20-22), our previous studies have shown that, unlike any other bunyavirus NSs, the SFTS virus NSs interacts with and relocalizes TBK1, RIG-I, and TRIM25 into endosome-like structures (18). Thus, SFTS virus appears to use a different mechanism for virus replication and inhibition of IFN responses than those described for other bunyaviruses.

SUMMARY OF THE APPLICATION

Studies aimed at characterizing early events of the phlebovirus replication cycle have shown that the prototype member, UUKV, enters the cells through a clathrin-independent mechanism. Specifically, UUKV has been shown to use $Rab5a^+$ early endosomes and later $Rab7a^+$ and $LAMP-1^+$ endosomes, suggesting that after entry the virus is directed toward the classical endosomal pathway (23). Interestingly, our studies have also shown that the SFTS virus NSs-positive cytoplasmic structures colocalize with Rab5, but not with Rab4 (18). Furthermore, we found that LC3, an important marker for autophagy, also colocalizes with these NSs-cytoplasmic structures; however, these structures were still observed in cells lacking Atg7, a gene essential for conventional autophagy (18, 24). We hypothesized that these SFTS virus NSs-positive structures were not conventional autophagosomes but rather they are derived from the endosomal pathway. Due to the role that these structures play in viral replication and evasion of host innate immunity, we have investigated the sources and the trafficking of these structures within the cells. Surprisingly, we observed that some of the SFTS virus NSs-positive structures were secreted into the extracellular space and were taken up by neighboring cells. Furthermore, we also demonstrated that these structures possess markers associated with extracellular vesicles and they contain infectious virions that were efficiently transported by these secreted structures into uninfected cells and were able to sustain efficient replication of the SFTS virus.

Provided herein is an isolated exosome. In one embodiment, an exome includes a nonstructural (NSs) protein of a virus that is a member of the Order Bunyavirales, or an active fragment thereof. In one embodiment, an exosome includes a fragment of an NSs protein of a virus that is a member of the Order Bunyavirales, and a domain. In one embodiment, an exosome includes a glycoprotein (Gn protein), or an active fragment thereof. In one embodiment, an exosome includes a fusion protein including a fragment of a Gn protein and a domain. An exosome can be CD63 positive. In one embodiment, an exosome can include both a Gn protein and a NSs protein. The Gn protein can be from a virus that is a member of the Order Bunyavirales In one embodiment, the member of the Order Bunyavirales is a member of the genus *Phlebovirus*. In one embodiment, the member of the genus *Phlebovirus* is Severe Fever with Thrombocytopenia Syndrome (SFTS) virus. In one embodiment, an exosome does not include a Severe fever with thrombocytopenia syndrome (SFTS) virus, and in another embodiment, the exosome further includes a SFTS virus genome.

In one embodiment, the exosome further includes a polynucleotide, such as a mRNA, tRNA, rRNA, siRNA, microRNA, non-coding RNA, coding RNA, or DNA. The DNA polynucleotide can include a coding region.

In one embodiment, the domain includes immunogenic activity, anti-cancer activity, anti-viral activity, anti-bacterial activity, or a combination thereof.

In one embodiment, the NSs protein has at least 85% similarity with SEQ ID NO:1. In one embodiment, the NSs protein includes SEQ ID NO:1.

In one embodiment, the Gn protein has at least 85% similarity with SEQ ID NO:2. In one embodiment, the Gn protein includes SEQ ID NO:2.

Also provided herein is a method for making an exosome. In one embodiment, the method includes incubating an engineered cell under conditions suitable for production of an exosome. The engineered cell can include an exogenous polynucleotide encoding a NSs protein of a virus that is a member of the Order Bunyavirales, or an active fragment thereof. The method can further include isolating the exosome. In one embodiment, the virus is a member of the genus *Phlebovirus*, such as SFTS virus. In one embodiment, the NSs protein has at least 85% similarity with SEQ ID NO:1.

Further provided herein is a method for delivering an agent to a cell. In one embodiment, the method includes contacting a cell with an exosome described herein, where the exosome includes an agent. The cell can be an ex vivo cell or it can be an in vivo cell. In one embodiment, the agent is delivered to the central nervous system. The agent can include a therapeutic agent, such as a vaccine or a drug. In one embodiment, the vaccine includes a protein. In one embodiment, the vaccine includes a polynucleotide that includes a coding region.

Also provided herein is a method for inducing an immune response in a subject. In one embodiment, the method includes administering to a subject an exosome described herein, where the exosome includes an immunogenic agent, such as a protein.

Further provided herein is a method for treating a condition in a subject. In one embodiment, the method includes administering to a subject in need thereof an exosome described herein, where the exosome includes an agent, such as a protein, suitable for treatment of a condition in the subject.

As used herein, the term “protein” refers broadly to a polymer of two or more amino acids joined together by peptide bonds. The term “protein” also includes molecules which contain more than one protein joined by disulfide bonds, ionic bonds, or hydrophobic interactions, or complexes of protein that are joined together, covalently or noncovalently, as multimers (e.g., dimers, tetramers). Thus, the terms peptide, oligopeptide, and polypeptide are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the term “polynucleotide” refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences such as regulatory sequences. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment.

As used herein, an “exogenous polynucleotide” refers to a polynucleotide that is not normally or naturally found in a cell. An exogenous polynucleotide includes a coding region that is not normally found in a cell, and a coding region that is normally found in a cell but is operably linked to a regulatory region to which it is not normally linked.

An “isolated” exosome is one that has been removed from a biological source of from a medium taken from cultured cells. For instance, an isolated exosome is an exosome that has been removed from a conditioned medium and many of the other biological components present in the medium, e.g., proteins, polynucleotides, and other cellular material of medium are no longer present.

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate protein is the protein being compared to the reference protein. A candidate protein can be isolated, for example, from a microbe, or can be produced using recombinant techniques, or chemically or enzymatically synthesized.

Unless modified as otherwise described herein, a pair-wise comparison analysis of amino acid sequences can be carried out using the BESTFIT algorithm in the GCG package (version 10.2, Madison Wis.). Alternatively, proteins may be compared using the Blastp program of the BLAST 2 search algorithm, as described by Tatiana et al. (*FEMS Microbiol Lett,* 174:247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent “identity” or may be referred to by percent “similarity.” “Identity” refers to the presence of identical amino acids. “Similarity” refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a protein containing deletions or additions of one or more contiguous or noncontiguous amino acids that do not eliminate a functional activity—such as, for example, immunological activity—of the protein are also contemplated.

Thus, as used herein, reference to a protein as described herein and/or reference to the amino acid sequence of one or more SEQ ID NOs can include a protein with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to a protein as described herein and/or reference to the amino acid sequence of one or more SEQ ID NOs can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

For any method disclosed herein that includes discrete steps, the steps may be conducted in any feasible order. And, as appropriate, any combination of two or more steps may be conducted simultaneously.

In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 1A-1D show SFTS virus NSs induces the formation of endosome-like structures. Ultrastructure analyses of SFTS virus NSs-expressing cells (FIG. 1A) and SFTS virus-infected cells (FIG. 1B) show cytoplasmic structures reminiscent of early endosomes (arrows) in ultrathin sections. Immunogold staining of distinct ultrathin sections shows cytoplasmic structures positive for SFTS virus NSs and Rab5 (FIG. 1C) or SFTS virus NSs and LC3B (FIG. 1D). Arrows indicate SFTS virus NSs in FIG. 8C and FIG. 8D, while triangles (in panel FIG. 1C and FIG. 1D) indicate the detection of Rab5 and LC3B, respectively. Ultrathin sections of mock-infected cells were also labeled, as indicated herein (not shown), to ensure the specificity of antibody. Representative images are shown.

(FIG. 3A) Schematic representation of the protocol for the isolation of secreted extracellular vesicles by ultracentrifugation. (FIG. 3B) Supernatants from cell lines expressing the mCherry and SFTS virus NSs-mCherry proteins were collected, and isolation of extracellular microvesicles was performed as indicated in FIG. 3A. The final pellet was resuspended in lysis buffer, sonicated, resolved by SDS-PAGE electrophoresis, transferred to a PVDF membrane, and blotted for SFTS virus NSs, LC3B, and common markers for microvesicles such as Rab5, β-tubulin, and CD63 (core protein, 26 kDa; glycosylated protein, 30 to 60 kDa). The cell monolayer was used to generate the whole-cell lysate (WCL) and assayed for the detection of the proteins indicated above. Densitometry analysis of CD63, LC3-I, and Rab 5 present in extracellular vesicles isolated from mCherry or SFTS virus NSs-mCherry expressing cells was also conducted. The band signal intensity of each protein was normalized to the signal intensity of β-tubulin and expressed as arbitrary units (A.U.). Signal intensities were obtained by using ImageJ software.

(FIG. 4A) Supernatant was collected, and isolation of extracellular microvesicles was performed as indicated.

(FIG. 4B) The final pellet was resuspended in lysis buffer, sonicated, resolved by SDS-PAGE electrophoresis, transferred to a PVDF membrane, and blotted for SFTS virus NSs, SFTS virus NP, and LC3B, in addition to common markers for microvesicles such as Rab5, CD63, and β-tubulin. The cell monolayer was used to generate the WCL and assayed for the detection of proteins indicated above. Densitometry analysis of CD63, LC3-I, and Rab 5 present in extracellular vesicles isolated from mock infected or SFTS virus-infected cells was carried out. The band signal intensity of each protein was normalized to the signal intensity of β-tubulin and expressed as arbitrary units (A.U.). Signal intensities were obtained by using ImageJ software.

(FIG. 5C) The number of CD63-positive and CD63/SFTS virus NSs-positive extracellular vesicles was quantified based on immunogold labeling observed from 10 fields of view. A total of 22 vesicles were observed in each experiment, of which an average of 14 were positive for both SFTS virus NSs and CD63. All electron microscopy experiments were repeated three times. Results are expressed as means plus the standard errors of the mean (SEM). Asterisks specify statistically significant difference ($P<0.05$) between the indicated groups.

(FIG. 6A) Extracellular vesicles were isolated as indicated in FIG. 4A, and samples were collected at each step of the purification process for evaluation by plaque assay. The sample resulting from the immune-selection step using anti-CD63 beads is depicted in the figure as the CD63 selected, whereas those resulting from the subsequent immune-(negative) selection step are shown as the CD63/SFTSV selected. As a final step, the purified vesicles were incubated with SFTS virus mouse hyperimmune ascitic fluid at a 1:1 ratio, and the antibody-virus complex was then removed with magnetic beads. A plaque assay of the resulting purified vesicles was performed, and the results are depicted in the figure as vesicles+anti-SFTS virus. The results of a plaque assay of the virus stock (infected cells from which the extracellular vesicles were derived) are shown as the SFTS virus stock. As a control, a virus stock was also subjected to the immune-negative selection step, followed by incubation with the SFTS virus antibody as indicated above, and a plaque assay was carried out (labeled "SFTS virus+anti-SFTS virus"). A dashed line indicates the limit of detection. The results are expressed as means+the SEM. Asterisks specify statistically significant differences ($P<0.05$) between the indicated groups. (FIG. 6B) An electron micrograph of isolated extracellular vesicles reveals the presence of virus-like particles contained within the vesicles (dark arrows). The presence of free virions from broken vesicles was also observed (light arrows).

(FIG. 8C) Percentages of cells positive for SFTS virus NP or NSs calculated by cell counts in 10 fields of view. A total of 150 cells were counted, and the percentage was calculated by dividing the total cells positive for SFTS virus NP or NSs by 150.

DETAILED DESCRIPTION OF ILLUSTRATIVE EMBODIMENTS

Figure 2:
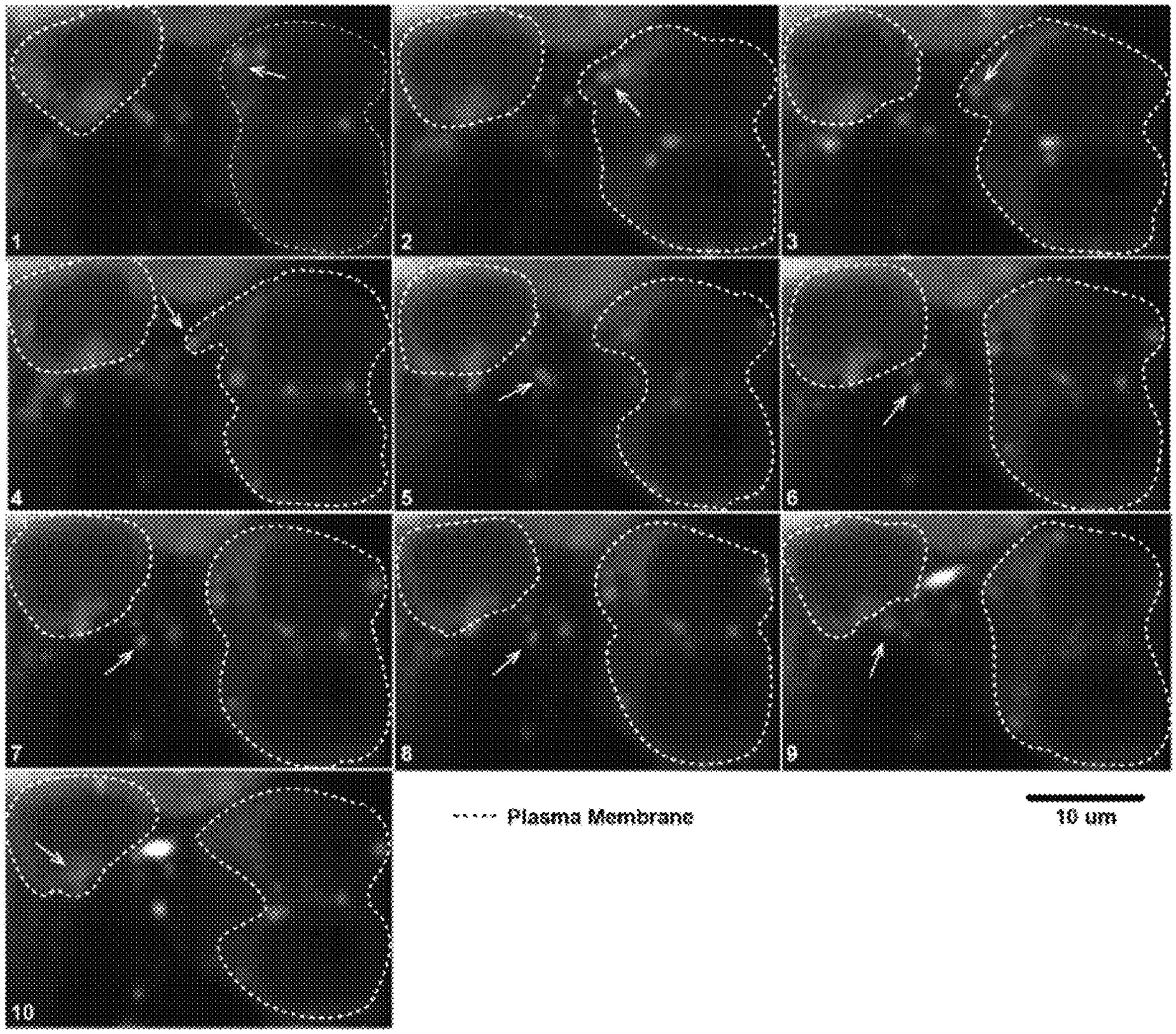
FIG. 2 shows cytoplasmic vesicles containing SFTS virus NSs-mCherry are secreted into the extracellular space and are endocytosed by neighboring cells. Live cell imaging was carried out in HeLa cell line stably expressing SFTS virus NSs-mCherry. Cells were visualized for 16 h using a Prairie Technologies/Nikon multimodal live cell imaging system. The arrow highlights the movement of the vesicle from cell to cell.

Provided herein are exosomes. As used herein, "exosome" refers to a membrane-enclosed vesicle, where the membrane is a bilayer. An exosome includes a compartment surrounded by the membrane. The size of an exosome described herein is at least 30 nanometers (nm), at least 40 nm, or at least 50 nm and no greater than 150 nm, no greater than 140 nm, no greater than 130 nm, no greater than 120 nm, no greater than 110 nm, or no greater than 100 nm. An exosome can be isolated.

An exosome can be positive for one or more markers. Examples of such markers include, CD63, CD9, CD82, and LC3-I. In one embodiment, an exosome is positive for CD63.

In one embodiment, an exosome includes a nonstructural protein (NSs) from a virus that is a member of the Order Bunyavirales, such as a member of the genus *Phlebovirus*. In one embodiment, the NSs is from a Severe Fever with Thrombocytopenia Syndrome (SFTS) virus. An example of a NSs is SEQ ID NO:1:

```
MSLSKCSNVDLKSVAMNANTVRLEPSLGEYPTLRRDLVECSCSVLTLSMVK

RMGKMTNTVTNWLFGNPKNPLHQLEPGLEQLLDMYYKDMRCYSQRELSALR

WPSGKPSVWFLQAAHMFFSIKNSWAMETGRENWRGLFHRITKGQKYLFEGD

MILDSLEAIEKRRLRLGLPEILITGLSPILDVALLQIESLARLRGLSLNHH
```

-continued

LFTSPSLRKPLLDCWDFFIPVRKKKTDGSYSVLDEDDEPGVLHGYPHLMAH

YLNRCPFHNLIRFDEELRTAALNTIWGRDWPAIGDLPKEV (also described at Genbank GI number gi|395406764, and Genbank Accession number YP_006504093.1).

A NSs protein present in an exosome can be an active fragment of a NSs protein. An active fragment of a NSs protein is one that mediates the production of exosomes by a cell and is associated with the produced exosome. In one embodiment, an active NSs fragment is one that increases production of exosomes by a cell. An active NSs fragment can be at least 50, at least 100, at least 150, at least 200, or at least 250 amino acids. Unless noted otherwise, reference herein to a NSs protein includes an active NSs fragment.

In one embodiment, an exosome includes a glycoprotein Gn from a virus that is a member of the Order Bunyavirales, such as a member of the genus *Phlebovirus*. In one embodiment, the Gn is from a Severe Fever with Thrombocytopenia Syndrome (SFTS) virus. An example of a Gn protein is SEQ ID NO:2:

DSGPIICAGPIHSNKSAGIPHLLGYSEKICQIDRLIHVSSWLRNHSQFQGY

VGQRGGRSQVSYYPAENSYSRWSGLLSPCDADWLGMLVVKKAKESDMIVPG

PSYKGKVFFERPTFDGYVGWGCGSGKSRTESGELCSSDSGTSSGLLPSDRV

LWIGDVACQPMTPIPEETFLELKSFSQSEFPDICKIDGIVFNQCEGESLPQ

PFDVAWMDVGHSHKIIMREHKTKWVQESSSKDFVCYKEGTGPCSESEEKAC

KTSGSCRGDMQFCKVAGCEHGEEASEAKCRCSLVHKPGEVVVSYGGTRVRP

KCYGFSRMMATLEVNPPEQRIGQCTGCHLECINGGVRLITLTSELRSATVC

ASHFCSSASSGKKSTEIHFHSGSLVGKTAIHVKGALVDGTEFTFEGSCMFP

DGCDAVDCTFCREFLKNPQCYPAKKWLFIIIVILLGYAGLMLLTNVLKAIG

VWGSWVIAPVKLMFAIIKKLMRTVSCLVGKLMDRGRQVIHEEIGENGEGNQ

DDVRIE (also described at Genbank GI number gi|395406767, and Genbank Accession number YP_006519138.1)

A Gn protein present in an exosome can be an active fragment of a Gn protein. An active fragment of a Gn protein is one that is associated with the produced exosome. An active Gn fragment can be at least 50, at least 100, at least 150, at least 200, at least 250, at least 300, at least 350, at least 400, at least 450, or at least 500 amino acids. Unless noted otherwise, reference herein to a Gn protein includes an active Gn fragment.

Other examples of an NSs protein and a Gn protein include those having structural similarity with SEQ ID NO:1 and SEQ ID NO:2, respectively. As used herein, a protein is “structurally similar” to a reference polypeptide if the amino acid sequence of the polypeptide possesses a specified amount of sequence similarity and/or sequence identity compared to the reference polypeptide (e.g., SEQ ID NO:1, SEQ ID NO:2, or a fragment thereof).

In one embodiment, a NSs protein is associated with the inner membrane of an exosome. In one embodiment, a Gn protein is associated with the outer membrane of an exosome. In one embodiment, an exosome includes both a NSs protein and a Gn protein.

A NSs protein or a Gn protein can be a fusion protein that includes amino acids from a NSs protein or a Gn protein and an additional amino acid sequence, also referred to herein as a domain. In one embodiment, the additional amino acid sequence may be useful for purification of the fusion polypeptide by affinity chromatography, such as a polyhistidine-tag (His-tag).

In one embodiment, an additional amino acid sequence has a biological activity. Examples of biological activity include, but are not limited to, immunogenic activity, anti-cancer activity, anti-viral activity, and anti-bacterial activity. An amino acid sequence fused to a NSs or a Gn protein can have more than one biological activity. The invention described herein that includes a fusion between either a NSs protein or a Gn protein and an additional amino acid sequence having biological activity is not limited to a particular additional amino acid sequence. Thus, any amino acid sequence having immunogenic activity, anti-cancer activity, anti-viral activity, or anti-bacterial activity can be fused to a NSs or Gn protein. Examples of additional amino acids having anti-cancer activity include, but are not limited to, Gomesin, PTP7. Examples of additional amino acids having antiviral activity include, but are not limited to, Viperin.

In one embodiment, the number of amino acids added to a NSs protein or a Gn protein can be at least 50, at least 100, at least 150, at least 200, at least 250, at least 300, at least 350, at least 400, at least 450, or at least 500 amino acids. In one embodiment, the number of amino acids added to a NSs protein or a Gn protein can be no greater than 600 amino acids, no greater than 550 amino acids, or no greater than 500 amino acids. In one embodiment, the additional amino acids added to a NSs protein or a Gn protein are at the amino terminal end or the carboxy terminal end of the NSs or Gn protein, and optionally at both ends of the NSs or Gn protein. In one embodiment, the additional amino acids added to an internal region of a NSs protein or a Gn protein.

An exosome described herein can include one or more other agents. Such an agent can be a therapeutic agent or a non-therapeutic agent. Examples of agents include, but are not limited to, a polynucleotide, a protein, and a small molecule. Examples of DNA polynucleotides include, but are not limited to, double stranded or single stranded molecules, and a coding region optionally with an operably linked regulatory region. Examples of RNA polynucleotides include, but are not limited to, mRNA, tRNA, rRNA, siRNA, microRNA, and ribozyme. Examples of small molecules include organic and inorganic compounds. A small molecule can have a biological activity such as decreasing symptoms or signs in a subject associated with a condition. A small molecule can be useful as an imaging agent such as, without limitation, positive or negative contrast agents (e.g., gadolinium or magnetic particles), fluorescent agents, dyes (e.g., calcein dye), radio imaging agents.

In one embodiment, the agent is associated with the inner aqueous compartment within an exosome. Methods for introducing an agent into exosomes are known to the skilled person. For instance, methods for introducing a polynucleotide into exosomes are described by Lotvall (U.S. Pat. No. 9,085,778). Alternatively, an agent, such as a protein or a polynucleotide, present in the cytoplasm of the cell making the exosome is passively included as a cargo in the exosome.

In one embodiment, the agent is associated with the membrane of the exosome. For instance, an agent can be inserted into the membrane. An example of such an agent is a transmembrane protein. Amino acids of a transmembrane protein can be exposed to the inner compartment of an exosome, the outer surface of an exosome, or the combination thereof.

In one embodiment, an agent is associated with the outer surface of an exosome. An example of a protein associated with the outer surface includes, but is not limited to, an antibody that specifically identifies, and is bound to, a surface epitope. Examples of surface epitopes include, but are not limited to, a CD63 epitope, a Gn protein epitope, or an epitope of any other antigenic molecule present on the surface of an exosome described herein. In one embodiment, the association of an agent with the surface of an exosome is covalent. Methods for modifying the surface of vesicles, such as virus like particles, are known and can be used to modify the surface of an exosome.

In one embodiment, an agent associated with the outer surface of an exosome can aid in targeting an exosome to a specific cell type. Such an agent is referred to herein as a "targeting group." A targeting group is a chemical species that interacts, either directly or indirectly, with a specific target. The targeting group can be, without limitation, a protein such as an antibody, or other molecule that interacts with a specific target. The "target" is a molecule present on the surface of a cell, e.g., a receptor. A cell presenting a target is also referred to herein as a "targeted cell."

An exosome described herein can include a SFTS genome or virion, and in one embodiment an exosome does not include an SFTS genome or virion.

Also provided herein is a cell that is engineered to include a NSs protein, a Gn protein, or a combination thereof. Examples of cells include eukaryotic cells, such as a cell from a primate (including a human cell), and a cell from a murine animal (including mouse and rat). The cell is one that has been removed from the body of an animal, and includes, for instance, primary cells (e.g., cells that have recently been removed from a subject and are capable of limited growth in tissue culture medium), and cultured cells (e.g., cells that are capable of long term culture in tissue culture medium). Specific examples of cell types include, but are not limited to, an epithelial cell, a B lymphocyte, a T lymphocyte, a mast cell, and a dendritic cell. In one embodiment, the cell is from a healthy individual. In another embodiment, the cell is from a diseased tissue. For instance, the cell can be a cancer cell.

A cell engineered to include a NSs protein or a Gn protein refers to a cell into which has been introduced an exogenous polynucleotide and has been altered by human intervention. The exogenous polynucleotide includes a coding region encoding the protein, and optionally additional amino acids when the protein is a fusion. The coding region includes nucleotides that encode a NSs protein or a Gn protein. It should be understood that a polynucleotide encoding a NSs protein represented by SEQ ID NO:1 or an NSs having structural similarity to SEQ ID NO:1, or a polynucleotide encoding a Gn protein represented by SEQ ID NO:2 or a Gn having structural similarity to SEQ ID NO:2, includes the class of polynucleotides encoding such a protein. The class of nucleotide sequences encoding a selected protein sequence is large but finite, and the nucleotide sequence of each member of the class can be readily determined by one skilled in the art by reference to the standard genetic code, wherein different nucleotide triplets (codons) are known to encode the same amino acid.

An exogenous polynucleotide introduced into a cell can include a vector in addition to a coding region encoding a NSs protein or Gn protein. A vector is a replicating polynucleotide, such as a plasmid, viral, or cosmid, to which another polynucleotide may be attached so as to bring about the replication of the attached polynucleotide. Construction of vectors containing a coding region encoding a NSs or Gn protein employs standard ligation techniques known in the art. See, e.g., Sambrook et al, *Molecular Cloning: A Laboratory Manual.*, Cold Spring Harbor Laboratory Press (1989) or Ausubel, R. M., ed. *Current Protocols in Molecular Biology* (1994). A vector can provide for further cloning (amplification of the polynucleotide), i.e., a cloning vector, or for expression of the polypeptide encoded by the coding region, i.e., an expression vector. The term vector includes, but is not limited to, plasmid vectors, viral vectors, cosmid vectors, or artificial chromosome vectors.

A coding region present on an exogenous polynucleotide introduced into a cell can include an operably linked regulatory sequence that regulates expression of the coding region. Nonlimiting examples of regulatory sequences include promoters, transcription initiation sites, translation start sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

The inventors have found that the NSs protein enhances the secretion of exosomes by a cell. The inventors have also found that a NSs fusion is incorporated into exosomes. In one embodiment, a method for producing exosomes includes incubating a cell that is engineered to express a NSs protein under conditions suitable for production of exosomes. The cell can be one that makes exosomes before a polynucleotide encoding a recombinant NSs is introduced. The number of exosomes secreted by the cell can be increased by at least 10-fold, at least 25-fold, at least 50-fold, at least 75-fold, or at least 100-fold compared to the same type of cell that is not engineered in the same way.

Also provided herein is a cell culture system expressing a NSs protein, or a fusion protein that includes NSs amino acids, effective to result in increased production of exosomes under suitable conditions.

The method can further include isolating the exosomes produced. Methods for isolating exosomes are known in the art (for instance, see Vlassov, U.S. Pat. No. 9,347,087).

Provided are methods for using the exosomes described herein. In one embodiment, a method includes delivering an agent to a cell. The agent can be therapeutic or non-therapeutic. Therapeutic agents include, but are not limited to, vaccines and drugs. A vaccine results in an immune response, such as a humoral immune response, a cell mediated immune response, or a combination thereof, in the recipient that can result in a decrease of symptoms or signs associated with a condition. A drug is an agent that can result in a decrease of symptoms or signs associated with a condition and does not necessarily involve an immune response. Examples of a vaccine include a compound having immunogenic activity, such as a protein or a polynucleotide. Examples of a drug also include a protein or a polynucleotide, as well as small molecules.

A method for delivering an agent to a cell comprises contacting a cell with an exosome described herein under conditions suitable for uptake of the exosome by the cell. The cell can be ex vivo or in vivo. An "ex vivo" cell refers to a cell that has been removed from the body of an animal. Ex vivo cells include, for instance, primary cells (e.g., cells that have recently been removed from a subject and are capable of limited growth in tissue culture medium), and cultured cells (e.g., cells that are capable of long term culture in tissue culture medium). An "in vivo" cell refers to a cell that is within the body of a subject.

In one embodiment, a method includes inducing an immune response in a subject. The method includes administering to a subject an exosome described herein that includes an immunogenic agent.

In one embodiment, a method includes treating a condition in a subject. The subject is a mammal, such as a human. As used herein, the term "condition" refers to any deviation from or interruption of the normal structure or function of a part, organ, or system, or combination thereof, of a subject that is manifested by a characteristic symptom or set of symptoms. Conditions include, but are not limited to, cancers such as, for instance, breast cancer and lung cancer. Other conditions include, for instance, infection by a pathogen, such as a eukaryotic pathogen, bacterial pathogen, or viral pathogen. An example of a viral pathogen is SFTS virus. Typically, whether a subject has a condition, and whether a subject is responding to treatment, is determined by evaluation of symptoms and/or signs associated with the condition. As used herein, the term "symptom" refers to objective evidence of condition present in a subject. As used herein, the term "clinical sign" or, simply, "sign" refers to objective evidence of a condition. Symptoms and/or signs associated with conditions referred to herein and the evaluation of such symptoms and/or signs are routine and known in the art.

Treatment of a condition can be prophylactic (e.g., preventative) or, alternatively, can be therapeutic (e.g., initiated after the development of a condition). Treatment that is prophylactic, for instance, initiated before a subject manifests symptoms of a condition, is referred to herein as treatment of a subject that is "at risk" of developing a condition. An example of a subject that is at risk of developing a condition is a person having a risk factor, such as a genetic marker, that is associated with the condition. Another example of a subject at risk of developing a condition such as an infectious disease is a person present in an area where the condition has been diagnosed in at least one other person, or is traveling to an area where an infectious agent is endemic. Treatment can be performed before, during, or after the occurrence of a condition described herein. Treatment initiated after the development of a condition may result in decreasing the severity of the symptoms of one of the conditions, or completely removing the symptoms.

In one embodiment, a method is gene therapy. An exosome used in this embodiment includes a polynucleotide having a coding region that encodes a protein and can result in a decrease of symptoms or signs associated with a condition.

In one embodiment, a method is for delivering an agent across the blood brain barrier. In this embodiment, a method includes administering to a subject an exosome, wherein a component of the exosome is increased in the central nervous system (CNS), such as the extracellular fluid of the CNS, a tissue of the CNS, or a cell of the CNS.

In one embodiment, a method for using an exosome can include targeting one or more specific type of cells. In another embodiment, a method for using an exosome can include not targeting one or more specific types of cells, e.g., the exosome does not include a targeting group.

The present invention is illustrated by the following examples. It is to be understood that the particular examples, materials, amounts, and procedures are to be interpreted broadly in accordance with the scope and spirit of the invention as set forth herein.

Example 1

Severe fever with thrombocytopenia syndrome (SFTS) virus is a newly recognized member of the genus *Phlebovirus* in the order Bunyavirales. The virus was isolated from patients presenting with hemorrhagic manifestations and an initial case fatality rate of 12 to 30% was reported. Due to the recent emergence of this pathogen, there is limited knowledge on the molecular virology of SFTS virus. Recently, we reported that the SFTS virus NSs protein inhibited the activation of the beta interferon (IFN-β) promoter. Furthermore, we also found that SFTS virus NSs relocalizes key components of the IFN response into NSs-induced cytoplasmic structures. We conducted live cell imaging studies to gain further insight into the role and trafficking of these cytoplasmic structures during virus infection. We found that some of the SFTS virus NSs-positive cytoplasmic structures were secreted to the extracellular space and endocytosed by neighboring cells. We also found that these secreted structures isolated from NSs-expressing cells and SFTS virus-infected cells were positive for the viral protein NSs and the host protein CD63, a protein associated with extracellular vesicles. Electron microscopy studies also revealed that the isolated CD63-immunoprecipitated extracellular vesicles produced during SFTS virus infection contained virions. The virions harbored within these structures were efficiently delivered to uninfected cells and were able to sustain SFTS virus replication. Altogether, these results suggest that SFTS virus exploits extracellular vesicles to mediate virus receptor-independent transmission to host cells and open the avenue for novel therapeutic strategies against SFTS virus and related pathogens.

SFTS virus is novel bunyavirus associated with hemorrhagic fever illness. Currently, limited information is available about SFTS virus. In the present study, we demonstrated that extracellular vesicles produced by SFTS virus-infected cells harbor infectious virions. We sought to determine whether these "infectious" extracellular vesicles can mediate transmission of the virus and confirmed that the SFTS virions were efficiently transported by these secreted structures into uninfected cells and were able to sustain efficient replication of SFTS virus. These results have significant impact on our understanding of how the novel tick-borne phleboviruses hijack cellular machineries to establish infection and point toward a novel mechanism for virus replication among arthropod-borne viruses.

Materials and Methods

Cells, plasmids, and viruses. HeLa and Vero76 cells were obtained from ATCC and maintained with minimal essential Eagle medium (Lonza) supplemented with L-glutamine, 1% penicillin-streptomycin (Gibco), and 10% fetal bovine serum. Cells used in the isolation of secreted vesicles were grown in media containing 10% fetal bovine serum depleted of endogenous vesicles by ultracentrifugation at 100,000×g for 16 h. Human embryonic kidney cells (HEK 293T) were obtained from the American Type Culture Collection and maintained with Dulbecco minimal essential medium (Lonza) supplemented with L-glutamine, 1% penicillin-streptomycin, and 10% fetal bovine serum. The SFTS virus NSs plasmid was constructed by PCR using overlapping deoxyoligonucleotides corresponding to the published GenBank sequence (NC_018137.1) and has been described elsewhere (18). The SFTS virus NSs-mCherry was constructed using standard cloning techniques (18). The mCherry and the SFTS virus NSs-mCherry genes were then cloned into a third-generation lentivirus vector and used to generate lentiviruses. HeLa cells were transduce with the lentivirus particles and the mCherry and SFTS virus NSs-mCherry stable cell lines were generated by antibiotic selection and cloning of the mCherry fluorescent cells to select those with high level of protein expression as determined by confocal microscopy and Western blot analyses.

The SFTS virus strain used in this study was provided by the Chinese Center for Disease Control and Prevention and passaged twice in Vero76 cells to generate viral stocks for this study. Generation of viral stocks was performed in Vero76 cells, with titers determined by plaque assay as previously described (18, 25). A multiplicity of infection (MOI) of ~0.01 was used in all experiments involving virus infection, unless stated otherwise.

Transfections and immunoblotting. All transfections were carried using 500 ng of plasmid DNA and Lipofectamine 3000 (Invitrogen) according to manufacturer's established protocol. Transfected cells were lysed with NP-40 lysis buffer (150 mM NaCl, 1.0% NP-40, 50 nM Tris-Cl [pH 8.0]) containing complete protease inhibitor cocktail (Roche) at 16 to 24 h posttransfection. For immunoblotting, proteins were resolved by SDS-PAGE and subsequently transferred onto a 0.2-μm-pore size polyvinylidene difluoride (PVDF) membrane (Thermo Scientific). PVDF membranes were blocked for 1 h with 5% nonfat dry milk or 5% bovine serum albumin (BSA; Fisher) in Tris-buffered saline with 1% Tween 20 (TBS-T). Membranes were then incubated for 16 to 18 h at 4° C. with primary antibodies. After incubation, membranes were washed three times and incubated with anti-mouse or anti-rabbit secondary antibodies conjugated with horseradish peroxidase (HRP) for 1 h. Lastly, blots were developed by using Western Lightning ECL (Perkin-Elmer) substrate according to the manufacturer's protocol. The following primary antibodies were used for immunoblotting: rabbit anti-SFTS virus NSs (1:500; GenScript), mouse anti-SFTS virus NP (1:500), rabbit anti-CD63 (1:100; Abcam), mouse anti-β Tubulin (1:1,000; Abcam), rabbit anti-LC3 (1:1,000; Abcam), and rabbit anti-Rab5 (1:1,000; Abcam). The secondary antibodies used were donkey anti-rabbit IgG HRP-conjugated antibody (1:5,000) and sheep anti-mouse IgG HRP-conjugated antibody (1:5,000) from GE Healthcare. For the detection of the exosomal marker CD63, the purified extracellular vesicles were lysed and resolved under nondenaturing conditions in order to detect the glycosylated forms of CD63 according to the manufacturer's recommendations. For comparison purposes, both reduced and nonreduced samples were transferred onto PVDF membrane and Western blotting performed as indicated above.

Immunofluorescence. HeLa cells were seeded onto coverslips treated with 50 μg/ml mouse laminin I (Cutler) and infected according to standard procedures. The cells were then incubated overnight at 37° C. in 5% $CO_2$. The cells prepared for infection were infected with SFTS virus (MOI=0.5) for 24, 48, or 72 h, fixed with 4% paraformaldehyde for 30 min, and then permeabilized with 0.1% Triton-X (Sigma) for 10 min. The cells were then washed, and a blocking incubation step with 10% goat serum (Sigma) and 3% BSA (Thermo Scientific) was carried out. Next, cells were incubated with primary antibodies for 1 h. Cell nuclei were visualized with Hoechst 33342 (1:1,000; Invitrogen) or with TO-PRO-3 Iodide (Invitrogen) according to the manufacturer's protocol. The following Alexa Fluor-conjugated antibodies from Invitrogen were used: Alexa Fluor 488-goat anti-mouse or Alexa Fluor 594-goat anti-rabbit antibodies. All secondary antibodies were used at a 1:1,000 concentration, and samples were visualized with a Zeiss LSM510META laser scanning confocal microscope or Olympus spinning disc confocal microscope.

Live cell imaging. HeLa cells stably expressing the SFTS virus NSs-mCherry were plated on 35-mm glass bottom culture dishes (MatTek Corp.) and incubated overnight at 37° C. in 5% $CO_2$. Prior to live cell imaging, the cell culture medium was removed, cells washed with Dulbecco phosphate-buffered saline (DPBS), and live cell imaging solution (Invitrogen) was added. Cells were visualized for 16 h using a Prairie Technologies/Nikon multimodal live cell imaging system.

Isolation and purification of extracellular vesicles. Isolation of SFTS virus NSs-positive vesicles was first standardized in the stable cell line expressing the NSs fused to mCherry fluorescent protein. Cells were grown to 90% confluence for approximately 3 days, and supernatants were later collected and clarified by centrifugation. Cleared supernatant was concentrated using a 3,000 molecular weight cutoff value column (Sartorius) and voided of any cellular debris by centrifugation at 10,000×g for 30 min. Vesicles were then pelleted at 100,000×g for 90 min. To further purify the vesicles and remove any contaminant protein, the pellet containing the vesicles was washed with ice-cold phosphate-buffered saline (PBS) and repelleted at 100,000×g for 90 min. The pellets used for electron microscopy were resuspended in 100 μl of molecular-grade water. For Western blot analysis, the pellets were resuspended in 100 μl of NP-40 lysis buffer and sonicated for 1 min. For isolation and purification of vesicles produced during SFTS virus infection, the same centrifugation procedure was used. However, the final pellet was subjected to an immunoprecipitation step using magnetic beads coated with anti-CD63 antibody at 4° C. overnight. Beads were then washed with ice-cold PBS, and the $CD63^+$ vesicles were released by resuspension in elution buffer (100 mM glycine-HCl [pH 2.8]). To further ensure that the $CD63^+$ vesicles were free of SFTS virions not packaged into the vesicles, we carried out an immunoprecipitation (negative selection) step using magnetic beads coated with antibodies against SFTS virus, and the mix was incubated overnight. The supernatant containing the $CD63^+$ vesicles was then removed and incubated at 4° C. for 4 h with SFTS virus mouse hyperimmune ascitic fluid at a 1:1 ratio. The virus-antibody complex was then removed, and the clarified supernatant was used to infect HeLa cells as described below to determine the capacity of the $CD63^+$ vesicles in mediating transmission of SFTS virus. To verify that the above procedures were effective at removing SFTS virions that were not packaged within the extracellular vesicles, we used the same methodology (immunoprecipitation and incubation with antibodies against SFTS virus) using an SFTS virus stock (titer of $10^6$ PFU/ml). The resulting preparation was then used to infect HeLa cells as described below.

Infection of HeLa cells with purified extracellular vesicles. Adsorption of the purified vesicles was performed by overlaying the purified preparation onto cells and incubated at 37° C. for 1 h. Where indicated, HeLa cells were pretreated with 2 μg/ml of mouse anti-CD63, mouse IgG1, or mouse anti-SFTS virus antibodies for 1 h prior to overlaying the cells with the purified vesicles or infecting them with SFTS virus. Supernatants were collected at 0, 24, 48, and 72 h postinfection (hpi) and assayed by plaque assay.

Transmission electron microscopy (TEM). For ultrastructural analysis in ultrathin sections, infected cells were fixed for at least 1 h in a mixture of 2.5% formaldehyde prepared from paraformaldehyde powder and 0.1% glutaraldehyde in 0.05 M cacodylate buffer (pH 7.3) to which 0.03% picric acid and 0.03% $CaCl_2$ were added. The monolayers were washed in 0.1 M cacodylate buffer, and the cells were scraped off and processed further as a pellet. The pellets were postfixed in 1% $OsO_4$ in 0.1 M cacodylate buffer (pH 7.3) for 1 h, washed with distilled water, and en bloc stained with 2% aqueous uranyl acetate for 20 min at 60° C. The pellets were dehydrated in ethanol, processed through propylene oxide, and embedded in Poly/Bed 812 (Polysciences, Warrington, Pa.). Ultrathin sections were cut on Leica EM UC7 ultramicrotome (Leica Microsystems, Buffalo Grove, Ill.), stained with lead citrate, and examined in a Philips 201 transmission electron microscope at 60 kV.

For immunogold labeling of thin sections, infected cells were fixed for at least 2 h in a mixture of 2.5% formaldehyde prepared from paraformaldehyde powder and 0.1% glutaraldehyde in 0.05 M cacodylate buffer (pH 7.3), to which 0.03% picric acid and 0.03% $CaCl_2$ were added. The monolayers were washed in 0.1 M cacodylate buffer, and the cells were scraped off and processed further as a pellet. The pellets were en bloc stained with 2% aqueous uranyl acetate for 20 min at 60° C. The pellets were dehydrated in ethanol, processed through propylene oxide, and embedded in LR White (Polysciences). Ultrathin sections were then cut on a Leica EM UC7 ultramicrotome (Leica Microsystems). The sections were then labeled and incubated with mouse anti-SFTS virus NSs and rabbit anti-LC3 (1:20) or mouse anti-SFTS virus NSs and rabbit anti-Rab5 (1:20) primary antibodies for 1 h at room temperature and overnight at 4° C. The sections were next washed three times with 1% BSA in TBS and incubated with secondary antibody goat anti-rabbit labeled with 6 nm colloidal gold (1:20) and goat anti-mouse labeled with 15-nm colloidal gold (1:20) for 1 h. After being washed with water, the grids were fixed with glutaraldehyde for 5 min, washed with water again, and negatively stained with 2% aqueous uranyl acetate for 5 min. A final wash with water was performed three times, followed by staining with lead citrate for 30 s. They were examined with a Philips CM-100 transmission electron microscope at 60 kV.

For visualization of isolated microvesicles by electron microscopy, purified vesicles were adsorbed onto Formvar-carbon coated nickel grids for 15 min, washed three times with molecular-grade water, and negatively stained with 2% aqueous uranyl acetate. For immunogold labeling, the sample was first adsorbed onto nickel grids as previously described (18) and then incubated with rabbit anti-SFTS virus NSs and mouse anti-CD63 (1:10) antibodies for 1 h at room temperature in a wet chamber. The grids were next washed three times with 1% BSA in TBS and incubated with secondary antibody goat anti-mouse labeled with 6-nm colloidal gold (1:20) and goat anti-rabbit labeled with 15-nm colloidal gold (1:20) for 1 h. After being washed with water, the grids were fixed with glutaraldehyde for 10 min, washed with water again, and negatively stained with 2% aqueous uranyl acetate. The samples were examined with a Philips CM-100 transmission electron microscope at 60 kV.

Additionally, for ultrastructural analysis in ultrathin sections, purified vesicles were fixed overnight at 4° C. in a mixture of 2.5% formaldehyde prepared from paraformaldehyde powder and 0.1% glutaraldehyde in 0.05 M cacodylate buffer. The pellets were washed in cacodylate buffer, followed by postfixation in 1% $OsO_4$ for 1 h, washed, and en bloc stained with 2% aqueous uranyl acetate for 20 min at 60° C. The pellets were dehydrated in ethanol, processed through propylene oxide, and embedded in Poly/Bed 812 (Polysciences). For conventional TEM, SFTS virus-infected cells were fixed and processed the same way. For immunoelectron microscopy on ultrathin sections, postfixation was omitted and, after dehydration in 75% ethanol, the pellets were processed and embedded in LR White resin. Ultrathin sections were cut on a Leica EM UC7 ultramicrotome (Leica Microsystems), stained with lead citrate, and examined in a Philips CM-100 transmission electron microscope at 60 kV. Grids where then processed as mentioned above for immunostaining.

Statistical analysis. Statistical analyses were carried out using two-way analysis of variance for multiple comparisons to determine statistical differences in virus titers by plaque assay. The results of the electron microscopy experiments were analyzed by performing Student t tests. All analyses were done by using GraphPad Prism version 6.05 (GraphPad Software). A P value of $<0.05$ was considered significant.

Results

SFTS virus infection induces the formation of cytoplasmic structures reminiscent of early endosomes. SFTS virus infection induces the formation of cytoplasmic structures that play a role during SFTS virus replication and for evasion of innate immune responses (17, 18). Furthermore, these structures colocalize with the early endosomal marker Rab-5 and the autophagy marker LC3, but not with the endosomal marker Rab-4 (18). It was also reported that the formation of these cytoplasmic structures in SFTS virus-infected cells was dependent on lipid metabolism and that lipid droplets may play a role during SFTS virus infection (17). TEM studies were conducted to gain further insight into the sources, morphology, and composition of these cytoplasmic structures in HeLa cells stably expressing mCherry or SFTS virus NSs-mCherry. Electron microscopy studies were also conducted in SFTS virus-infected or mock-infected Vero cells. Consistent with our previous observations (18), TEM revealed the formation of structures reminiscent of early endosomes in cells stably expressing SFTS virus NSs, as well as in virus-infected cells (FIGS. 1A and B, respectively). Similar structures have also been described during UUKV infection (23). Additionally, we conducted immunogold electron microscopy on ultrathin sections of infected cells to substantiate that these structures were of endosomal origin. In correlation with our previous findings, we observed the colocalization of Rab5 and LC3 with the SFTS virus NSs-positive structures (FIGS. 1C and D, respectively).

SFTS virus NSs-positive structures are released into the extracellular space. In order to gain a better understanding on how these SFTS virus NSs-positive structures traffic within the cells, we conducted live cell imaging of HeLa cells expressing SFTS virus NSs-mCherry. This approach allows the direct observation of the SFTS virus NSs-cytoplasmic structures due to the fluorescent signal. Cells were plated and monitored for 16 h using a Prairie Technologies/Nikon multimodal live cell imaging system. Interestingly, we observed that a portion of the SFTS virus NSs structures were secreted into the extracellular space and were taken up by neighboring cells (FIG. 2). These data suggest that the released SFTS virus NSs cytoplasmic structures may be extracellular vesicles.

Figure 3A:
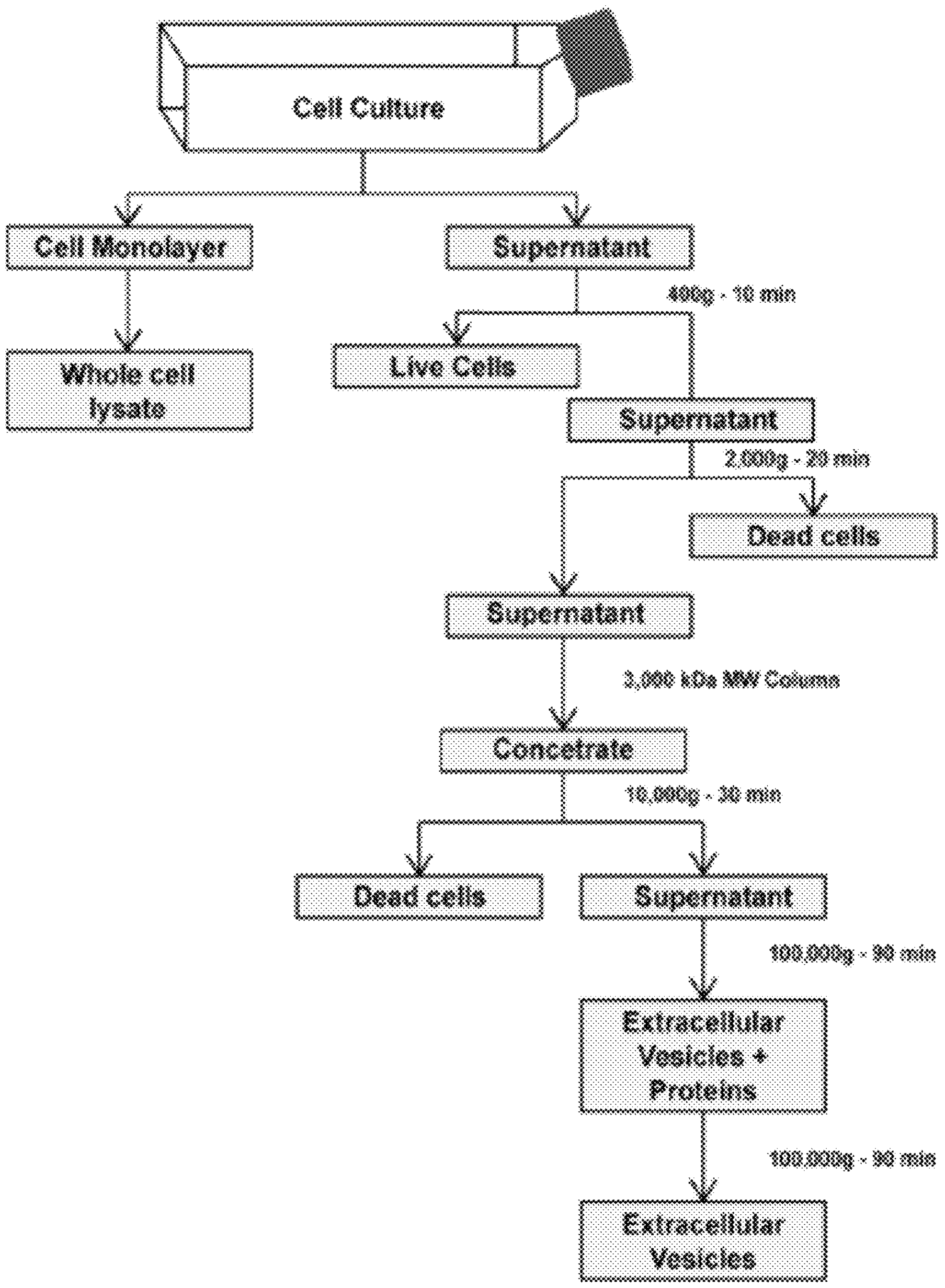
FIGS. 3A-3B show isolation and characterization of SFTS virus NSs-positive secreted extracellular vesicles.
Figure 3B:
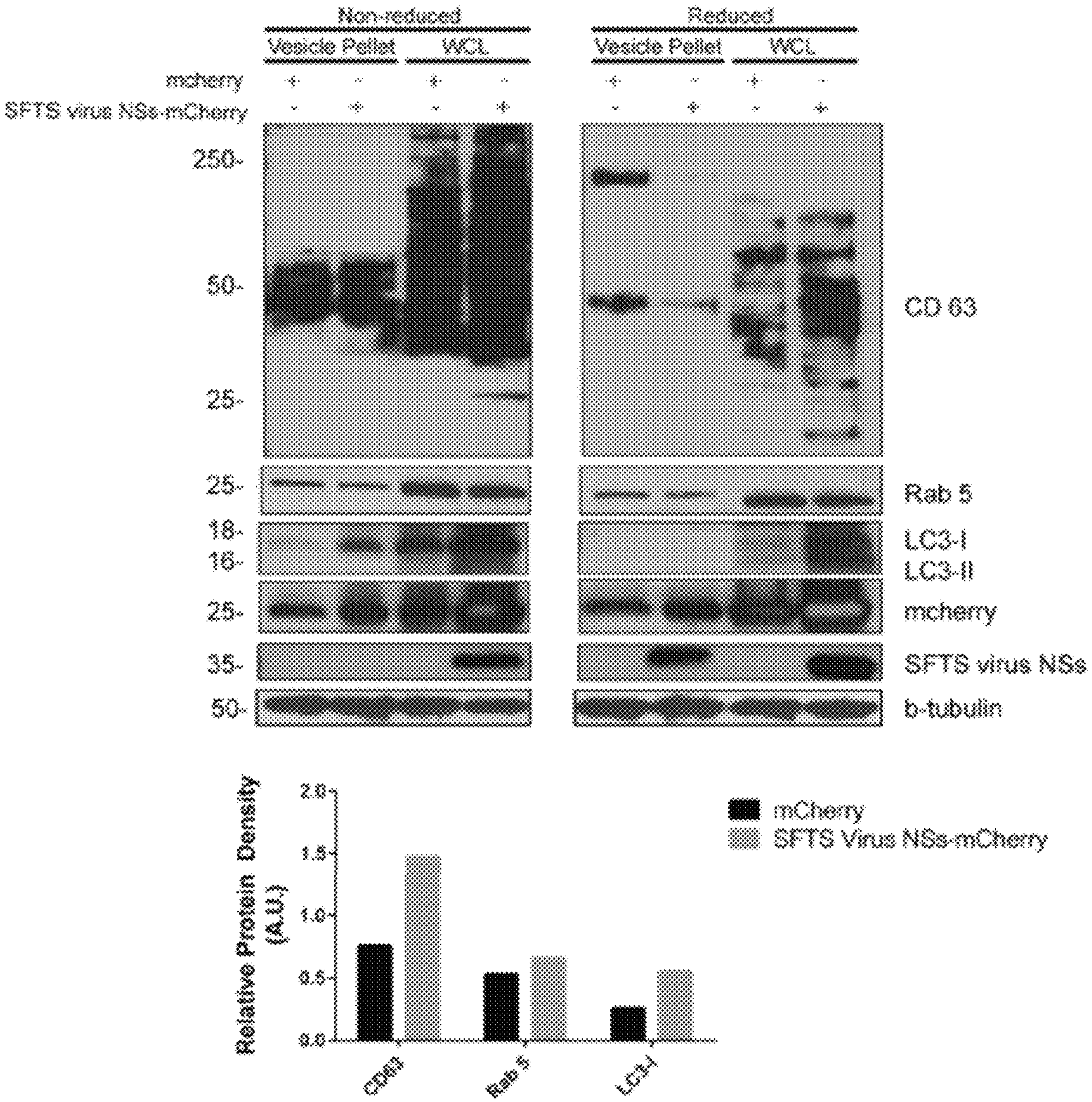
Figure 4A:
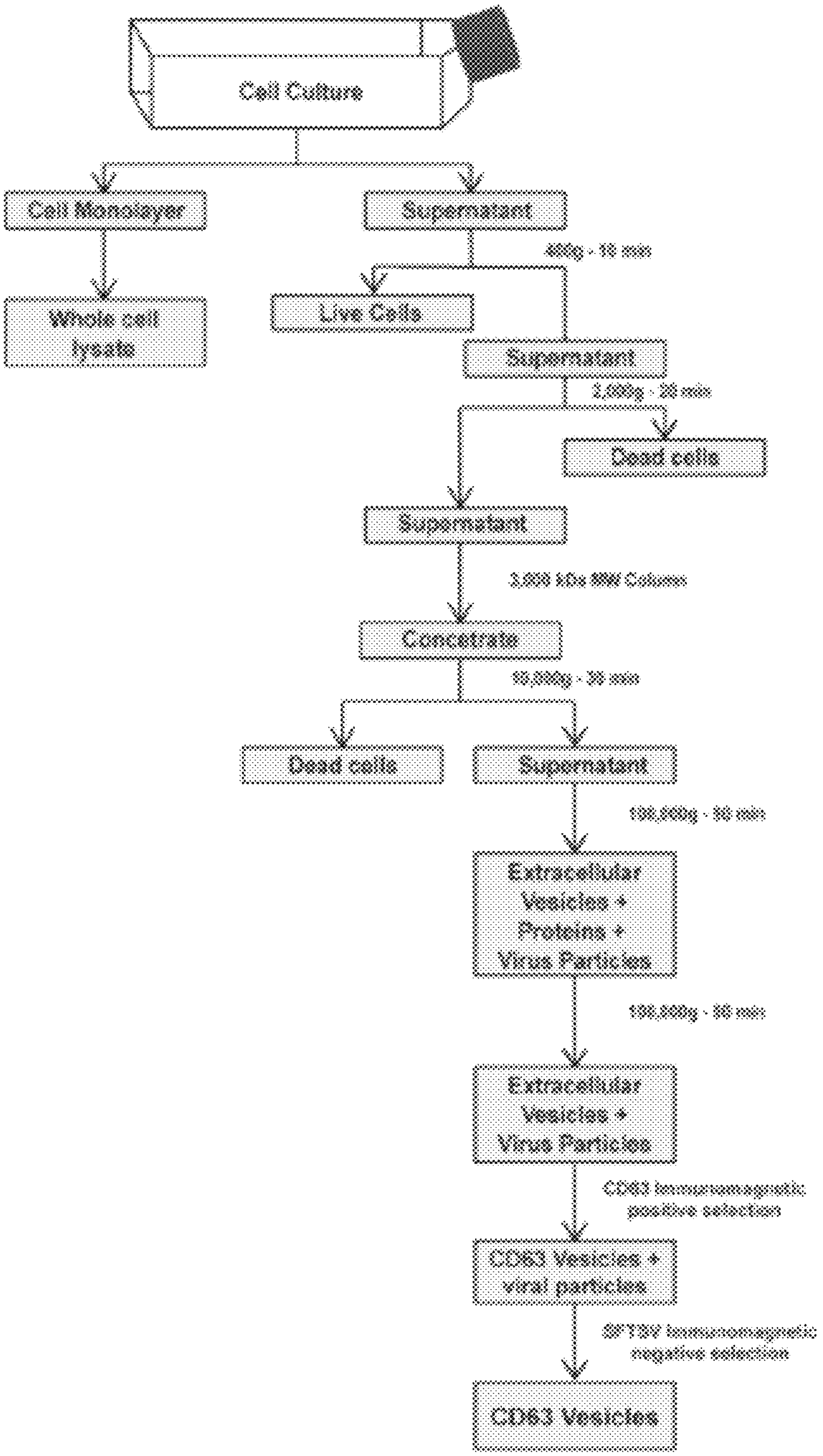
FIGS. 4A-4B show characterization of extracellular microvesicles secreted during SFTS virus infection. HeLa cells were mock infected or infected with SFTS virus for 72 h.
Figure 4B:
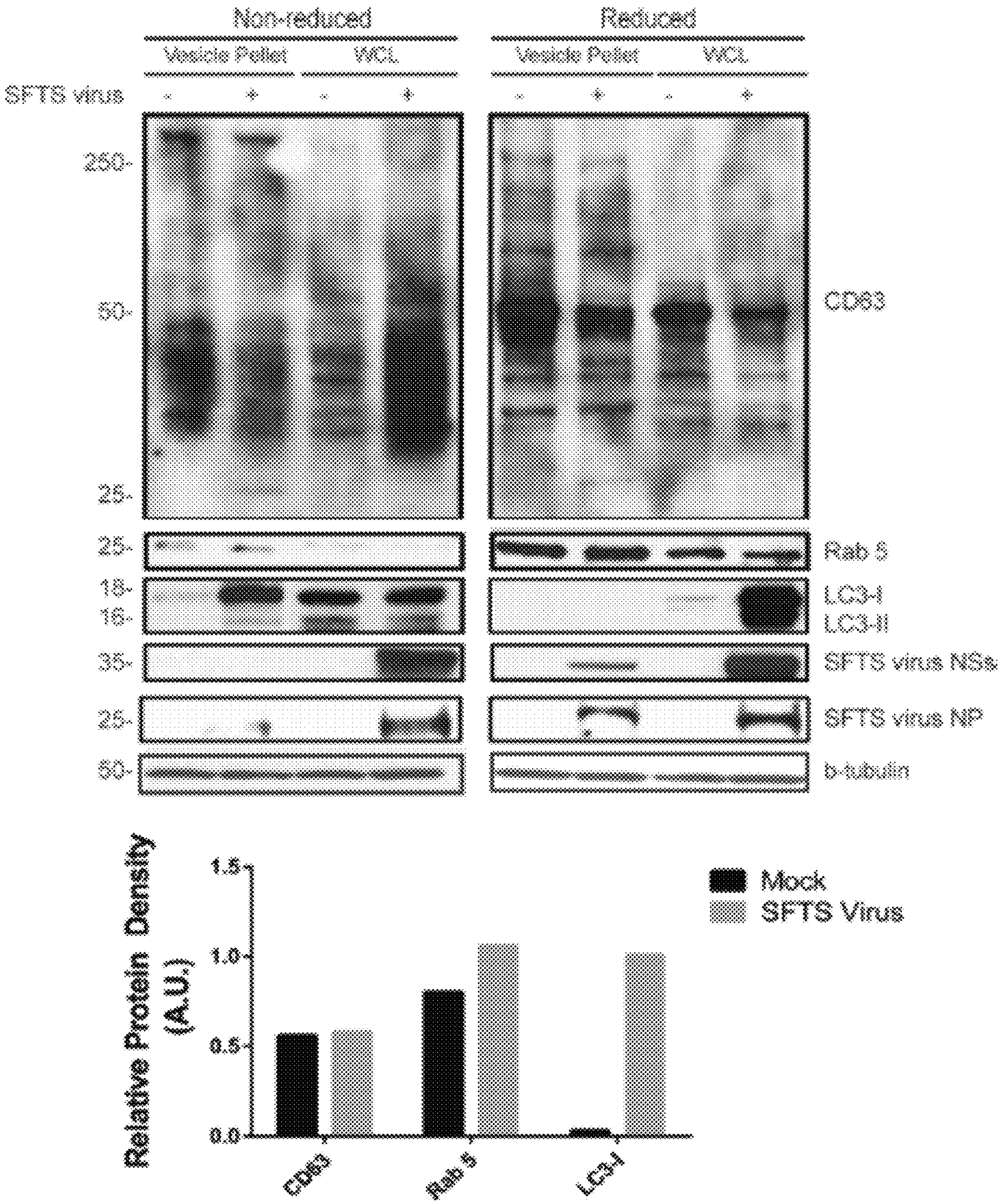

SFTS virus NSs-positive secreted structures contain markers found in extracellular vesicles. The release of extracellular vesicles has been shown to be an important mechanism for intercellular communication. These vesicles are generally referred to as exosomes (if they originated from multivesicular endosome) or microvesicles (if they originate from the plasma membrane) (26). In light of the results described above related to the involvement of the endosomal pathway in the formation of SFTS virus NSs-induced structures, as well as the active transfer of secreted SFTS virus NSs-positive structures into neighboring cells, we hypothesized that the cytoplasmic structures produced by SFTS virus NSs-expressing cells were exosomes. To test this hypothesis, we initially purified the extracellular vesicles produced by HeLa cells expressing mCherry and SFTS virus NSs-mCherry (as described in FIG. 3A) and carried out SDS-PAGE coupled with Western blotting to investigate the presence of tetraspanins such as CD63 that are known to be abundant in exosomes (27). Consistent with our hypothesis, the presence of CD63 was confirmed in the purified extracellular vesicles produced by SFTS virus NSs-mCherry expressing cells, as well as in cells expressing the mCherry protein (FIG. 3B). The presence of both Rab5 and LC3-I was also detected in the extracellular vesicles produced by both mCherry and SFTS virus NSs-mCherry expressing cells. It was also evident that in the presence of SFTS virus NSs, there was an increased amount of LC3-I and CD63 protein and a minor increase in the amount of Rab5 being incorporated into the extracellular vesicles. Densitometry analyses confirmed these observations (FIG. 3B, bottom panel). The increased detection of LC3-I also correlates with the increased amount of mCherry protein being detected in SFTS virus NSs-expressing cells, which may indicate that the SFTS virus NSs induces or enhances the production of extracellular vesicles (FIG. 3B). Furthermore, the mCherry protein was also detected in the extracellular vesicles, which could indicate that the mCherry protein may be mediating the incorporation of SFTS virus NSs into these vesicles rather than the viral protein. Therefore, we proceeded to investigate whether or not extracellular vesicles are produced during SFTS virus infection and determine if the SFTS virus NSs protein was incorporated within these vesicles, similar to what was found in NSs-expressing cells. The approach for the isolation and purification of the extracellular vesicles is described in FIG. 4A. Consistent with the results obtained in HeLa cells expressing the viral protein NSs, Western blot analyses revealed the presence of SFTS virus NSs, LC3-I as well as the endosomal marker Rab5 within the extracellular purified vesicles produced by SFTS virus-infected Vero cells (FIG. 4B). Densitometry analyses confirmed that there was increased amount of LC3 and Rab5 being incorporated into the vesicles but no CD63 (FIG. 4B, bottom panel). Furthermore, the viral nucleoprotein NP was also detected (FIG. 4B). These data provide evidence that SFTS virus NSs is incorporated within extracellular vesicles produced in NSs-expressing cells, as well as those produced during SFTS virus infection.

Figure 5B:
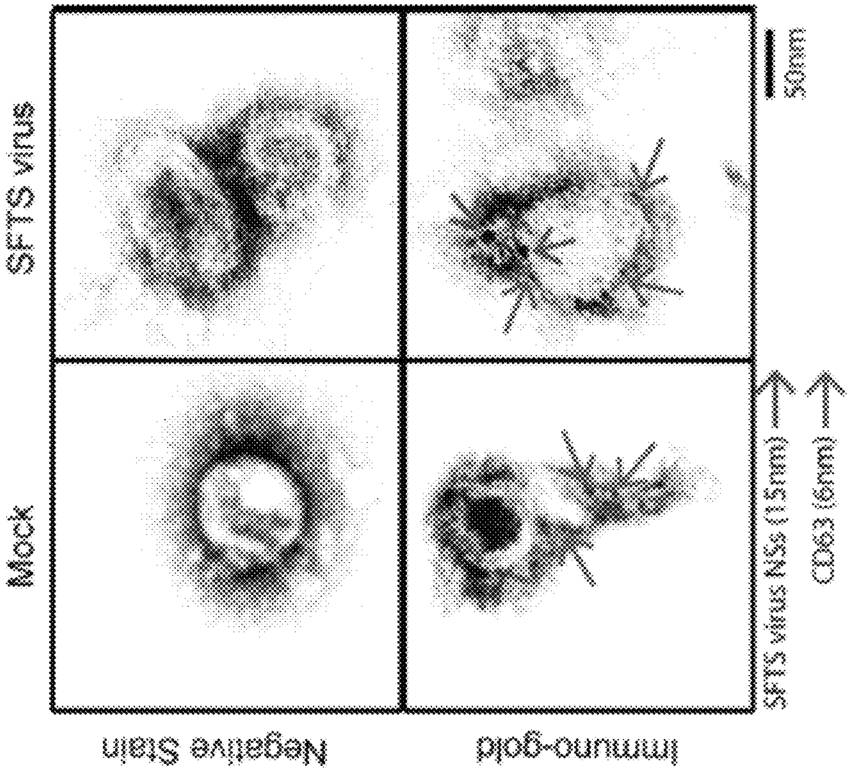
FIGS. 5A-5C show isolated extracellular vesicles are positive for SFTS virus NSs and the exosomal marker CD63. Supernatant was collected from HeLa cells stably expressing mCherry or SFTS virus NSs-mCherry (FIG. 5A) and from HeLa cells mock-infected or infected with SFTS virus (FIG. 5B), and isolation of extracellular microvesicles was performed as depicted in FIG. 3A. The final pellet was resuspended in molecular-grade water. The sample was adsorbed onto Ni grids and negatively stained with 2% aqueous uranyl acetate. Additional grids were incubated with primary antibodies against SFTS virus NSs (rabbit) and CD63 (mouse) and then secondary goat anti-mouse IgG couple to 6-nm colloidal gold and goat anti-rabbit IgG coupled to 15-nm colloidal gold antibodies and then negatively stained with 2% aqueous uranyl acetate. SFTS virus NSs is indicated by red arrows, and CD63 is indicated by green arrows.
Figure 5A:
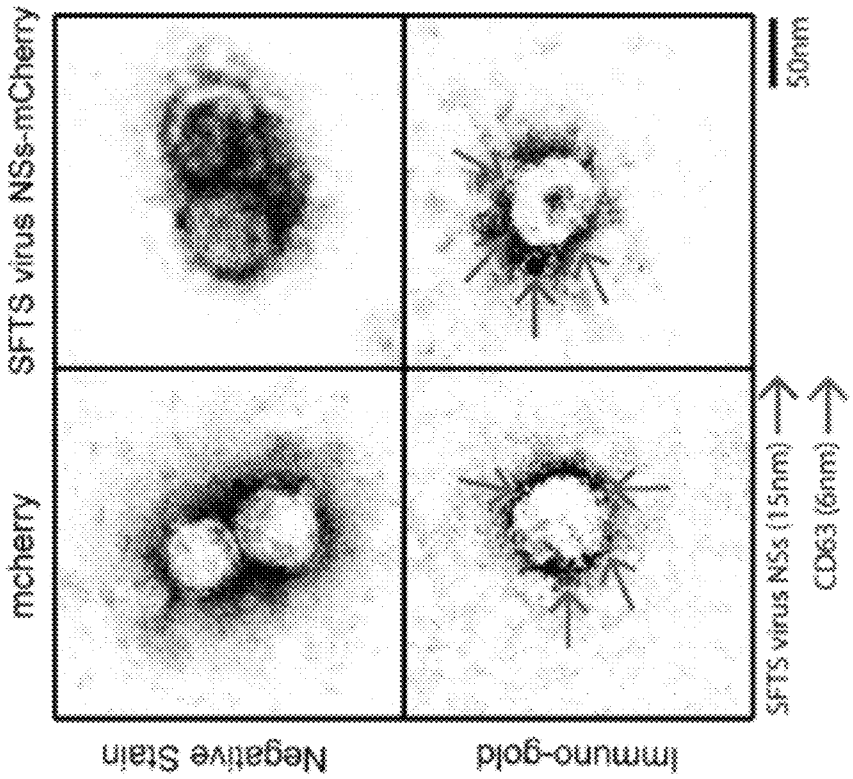
Figure 5C:
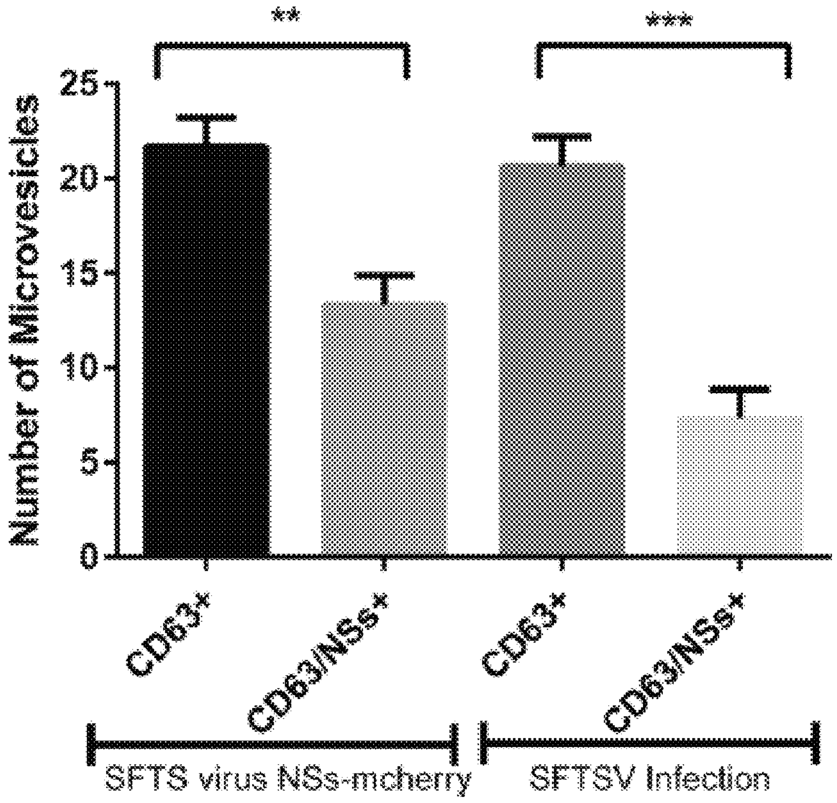

Ultrastructural analysis of purified SFTS virus NSs-positive extracellular vesicles. Extracellular vesicles are known to be secreted by most cell types (28). Thus, we next explored the possibility that the majority of the extracellular vesicles released in SFTS virus NSs-mCherry expressing cells and SFTS virus-infected cells harbor the NSs viral protein, which could suggest that SFTS virus directly targets the secretory multivesicular endosomal pathway. To evaluate this possibility, extracellular vesicles produced by HeLa cells expressing the mCherry or SFTS virus NSs-mCherry and SFTS virus-infected or mock-infected HeLa cells were purified and examined by electron microscopy and immunogold electron microscopy using antibodies against the SFTS virus NSs and CD63. Discrimination between these proteins after immunogold staining was done based on the size of the gold beads. The extracellular vesicles isolated from mCherry and mock-infected cells were only positive for the exosomal marker CD63 and were 50 to 100 nm in size, which is consistent with the normal 30- to 150-nm size range of exosomes (29, 30) (FIGS. 5A and B, left panels). The extracellular vesicles isolated from SFTS virus NSs-mCherry and SFTS virus-infected cells were positive for CD63 (FIGS. 5A and B, right bottom panels). Interestingly, the SFTS virus NSs protein (FIGS. 5A and B, right bottom panels) was detected in approximately 35 to 50% of these $CD63^+$ vesicles produced by NSs-expressing cells and SFTS virus-infected cells (FIG. 5C). No significant difference in size was observed among the extracellular vesicles whether they were positive for SFTS virus NSs or not. These results suggest that SFTS virus efficiently targets the secretory multivesicular endosomal pathway.

Figure 6A:
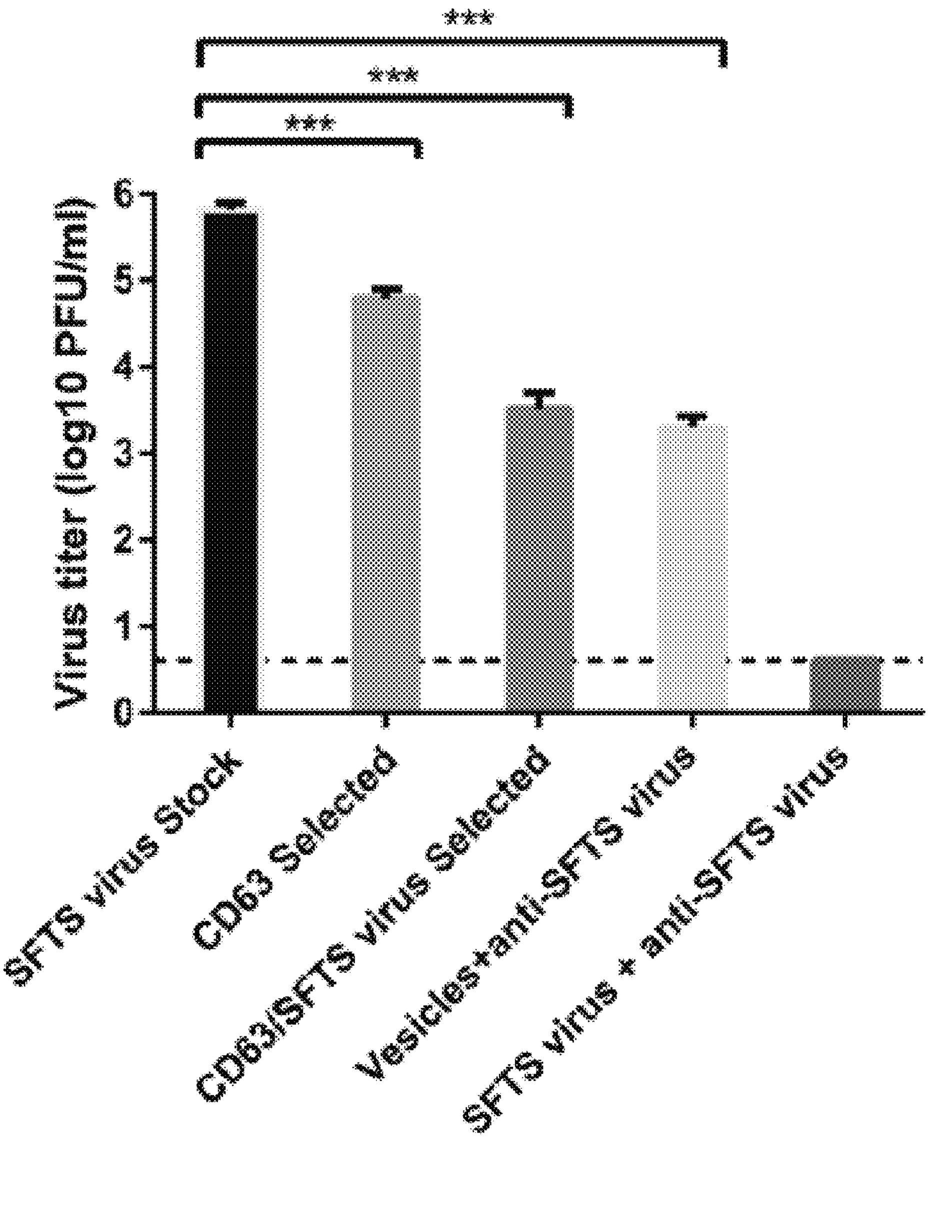
FIGS. 6A-6B show SFTS virus NSs-positive extracellular vesicles harbor infectious SFTS virus virions.
Figure 6B:
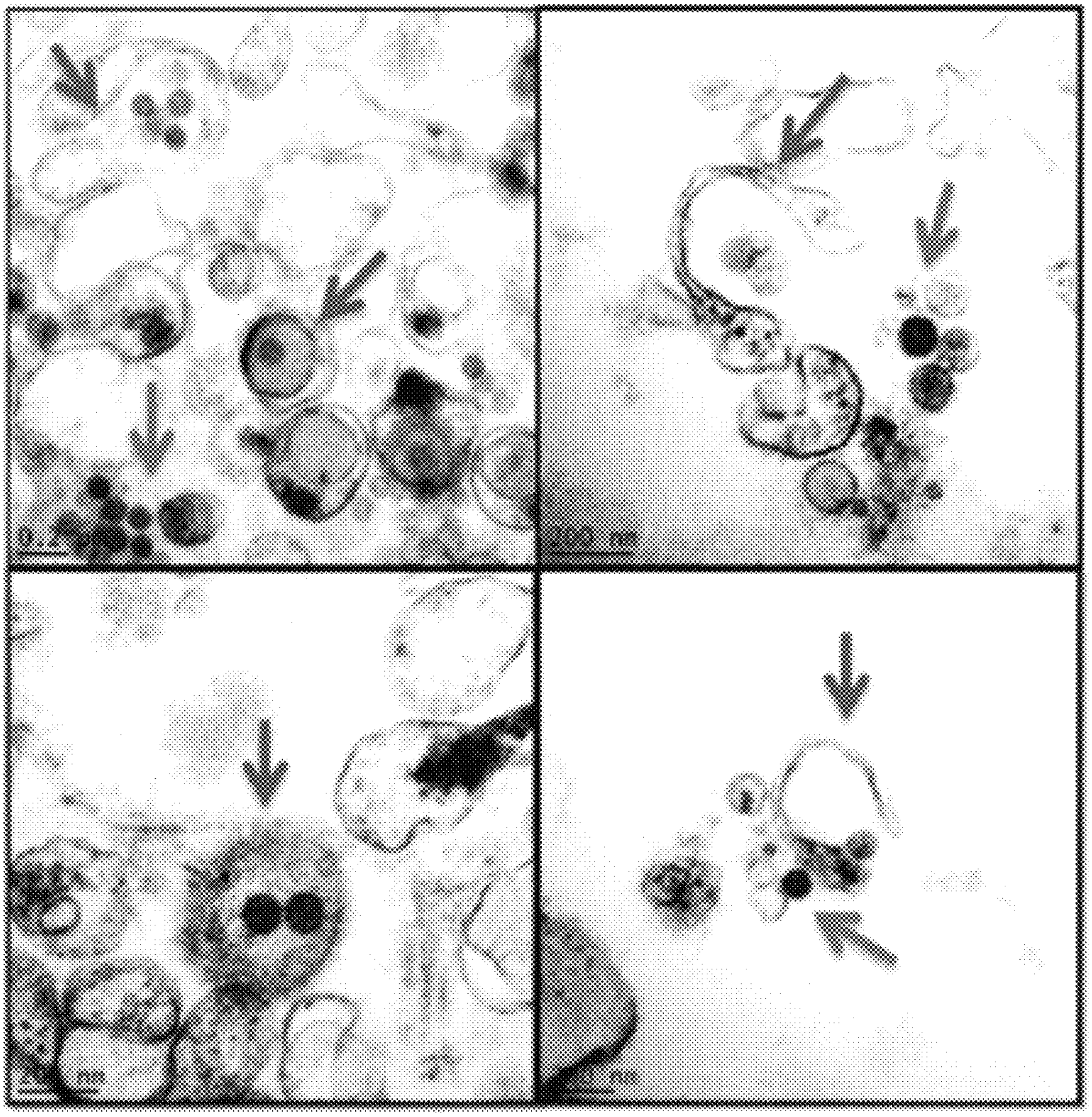

SFTS virus NSs-positive extracellular vesicles contain SFTS virions. Several studies have implicated the role of extracellular vesicles in many cellular processes, including tissue injury and immune responses, and for the transport of proteins, mRNA, and microRNAs (miRNAs) between cells (31). More recently, evidence has also been obtained for the role of extracellular vesicles in the transmission of infectious agents, as well as in the modulation of host immune responses to many pathogens (32-37). With regard to SFTS virus, a recent study suggested that the SFTS virus NSs-positive cytoplasmic structures play a role during SFTS virus replication on the basis of colocalization with viral RNPs and double-stranded RNA (17). In light of the results described above and the role of SFTS virus NSs cytoplasmic structures during virus replication, we next investigated if the extracellular vesicles released by SFTS virus-infected cells contained infectious virions. Extracellular vesicles produced during SFTS virus infection were purified as shown in FIG. 4A. Briefly, due to the possibility that the virions and extracellular vesicles may have similar sizes and densities and that our procedure would not completely devoid the extracellular vesicles from free virions (28, 38), we carried out an immune-selection step using anti-CD63 beads (FIG. 6A) as previously described (39), followed by a second immune(-negative) selection using magnetic beads coated with antibodies against SFTS virus (FIG. 6A). As a final step and to ensure removal of contaminant SFTS virions in our sample, the purified vesicles were incubated with SFTS virus mouse hyperimmune ascitic fluid at a 1:1 ratio (FIG. 6A). The antibody-virus complex was then removed with magnetic beads. The resulting purified vesicles were then used for plaque assay (FIG. 6A) and to infect HeLa cells (FIGS. 7A-7D). Notably we observed that the CD63-purified extracellular vesicles that underwent only immune-negative magnetic selection and those that were incubated with anti-SFTS virus hyperimmune ascitic fluid after immune-negative selection were able to produce viral titers of $4.5\times10^3$ PFU/ml and $2.5\times10^3$ PFU/ml, respectively (FIG. 6A). In contrast, the SFTS virus stock produced a titer of $7.5\times10^5$ PFU/ml whereas the extracellular vesicles that solely underwent CD63 positive immuno-magnetic selection produced a titer of $7.5\times10^4$ PFU/ml. This indicates that (i) centrifugation and CD63-positive immunoselection are not sufficient enough to void the vesicle preparation of free SFTS virions and (ii) purified extracellular vesicles produced by SFTS virus-infected cells are capable of mediating productive infection. We confirmed that our immune-negative selection step and further incubation with anti-SFTS virus antibodies was successful in removing virus particles not packaged into vesicles because our virus stock (titer of $10^6$ PFU/ml) was subjected to the same procedure and subsequently assayed by plaque assay and we were unable to detect viral plaques (FIG. 6A). Lastly, these data suggest that the extracellular vesicles contribute as much as 2 logs of infectious virus particles to the total viral titer (compare SFTS virus stock titer to CD63/SFTS virus selected vesicles). To further confirm that the extracellular vesicles contain infectious virions, vesicles were purified from SFTS virus-infected cells, as shown in FIG. 4A, and analyzed by electron microscopy, which revealed the presence of "virus-like particles" within the isolated vesicles (FIG. 6B). These data indicate that SFTS virus hijacks the secretory multivesicular endosomal pathway to possibly mediate transmission of the virus.

Figure 7A:
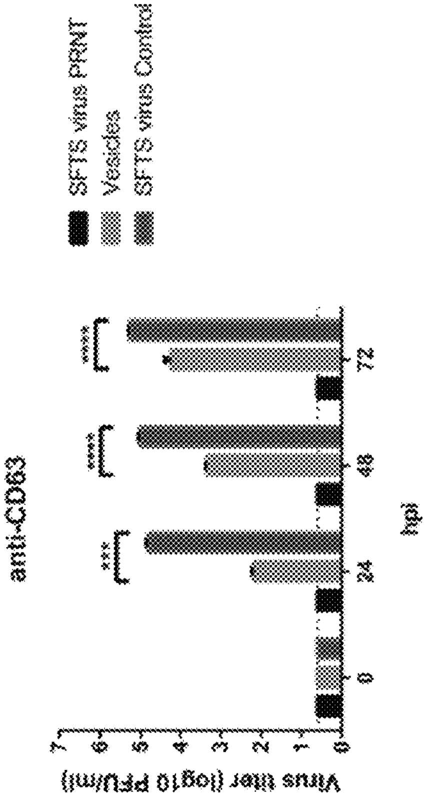
FIGS. 7A-7D show SFTS virus NSs-positive extracellular vesicles can mediate receptor-independent transmission of SFTS virus. HeLa cells were pretreated with anti-CD63 antibody (FIG. 7A), IgG control (FIG. 7B), anti-SFTS virus antibody (FIG. 7C), or PBS (FIG. 7D) prior to infection with the purified extracellular vesicles, SFTS virus, or the SFTS virus preparation subjected to the immune-negative selection and the antibody incubation step described in FIG. 6. Supernatants were harvested at 0, 24, 48, and 72 hpi, and a plaque assay was performed. The dashed line indicates the limit of detection (4 PFU/ml). All experiments were repeated three times with consistent results. The results presented are expressed as means+the SEM. Asterisks indicate statistically significant differences ($P<0.05$) between the indicated groups.
Figure 7B:
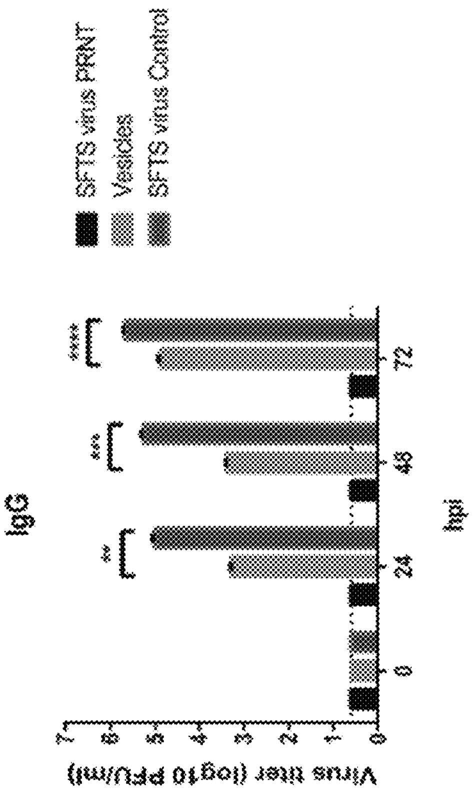
Figure 7C:
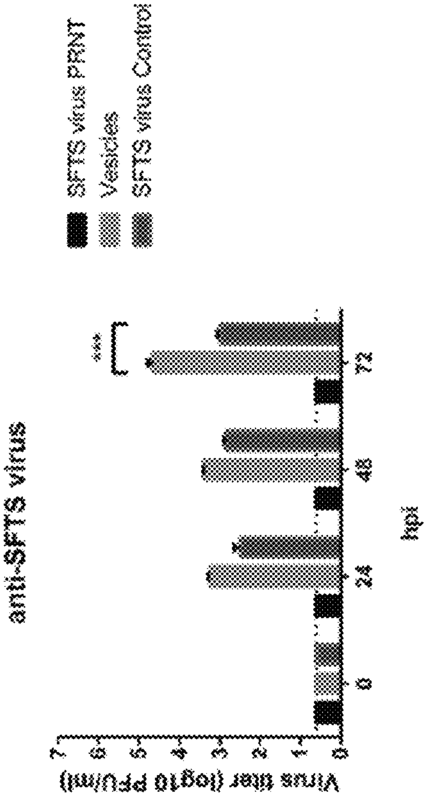
Figure 7D:
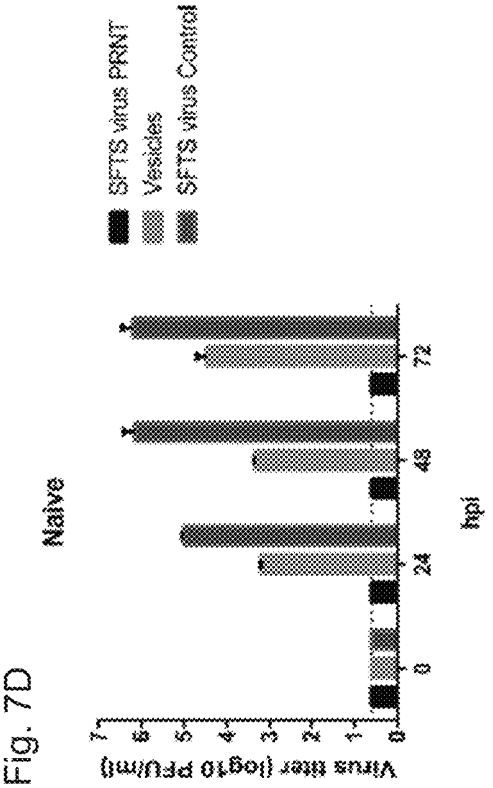
Figure 8A:
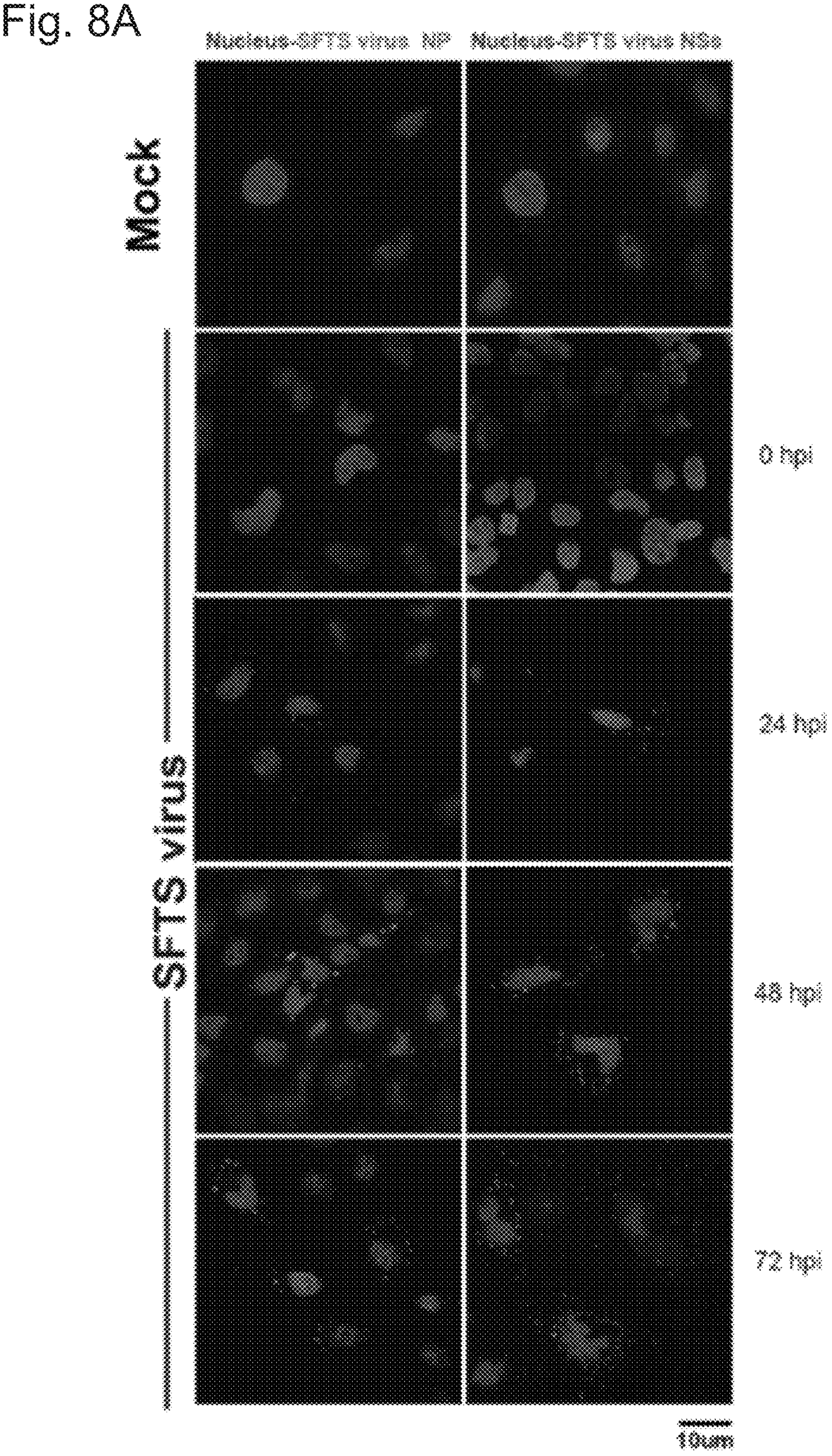
FIGS. 8A-8C show virions harbored within SFTS virus NSs-positive extracellular vesicles are capable of establishing productive infection. HeLa cells were mock infected (top of FIG. 8A and FIG. 8B), infected with SFTS virus (FIG. 8A), or infected with supernatants collected from cells infected with the purified, CD63 immune-selected extracellular vesicles described in FIG. 7D (FIG. 8B). Cells were fixed at 0, 24, 48, and 72 hpi. Immunofluorescence was performed using primary antibodies against SFTS virus NP or NSs and Alexa Fluor 488 as the secondary antibody. Nuclei were visualized with Hoechst 33342. Representative images for the mock-infected groups are shown.
Figure 8B:
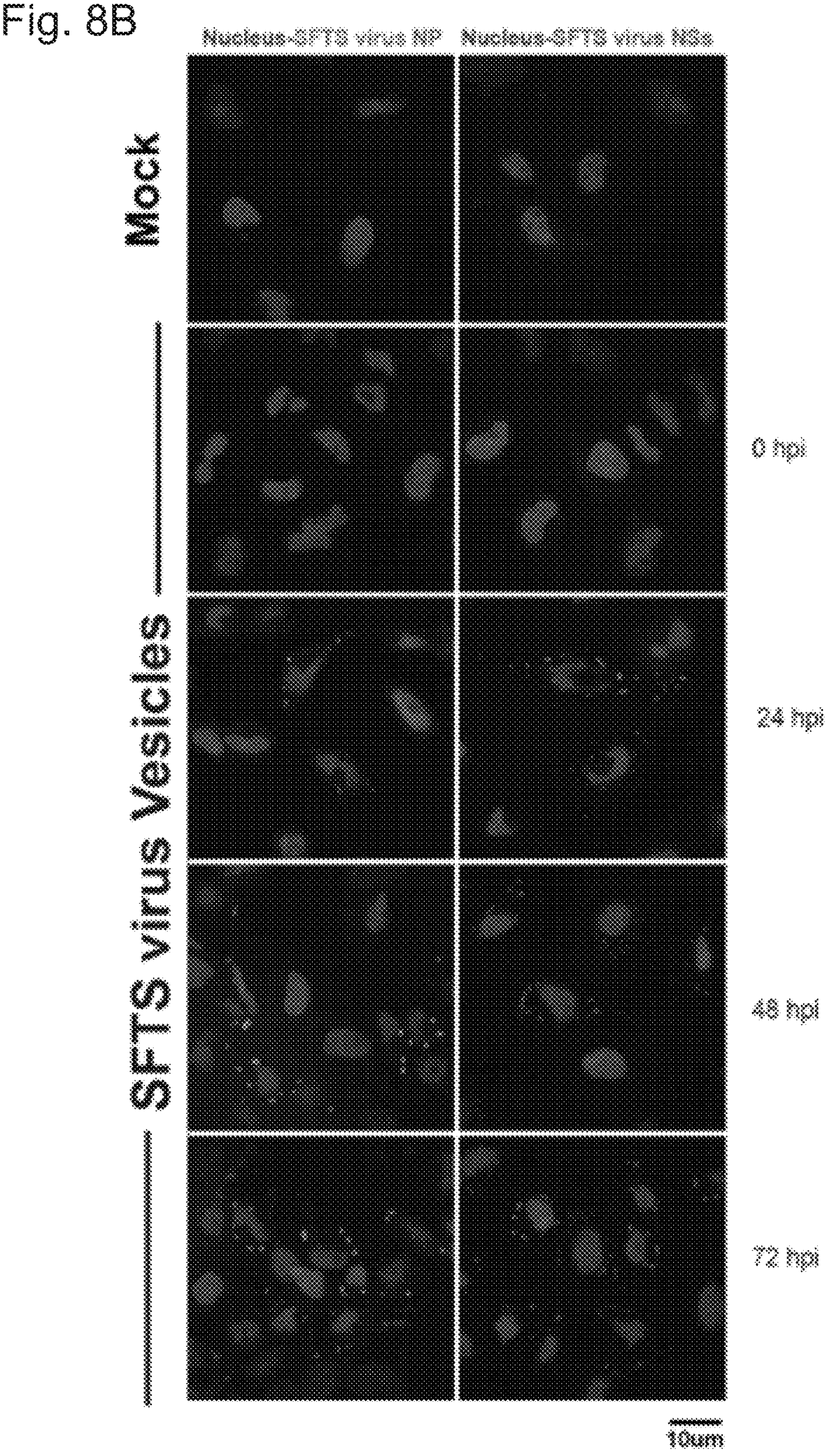
Figure 8C:
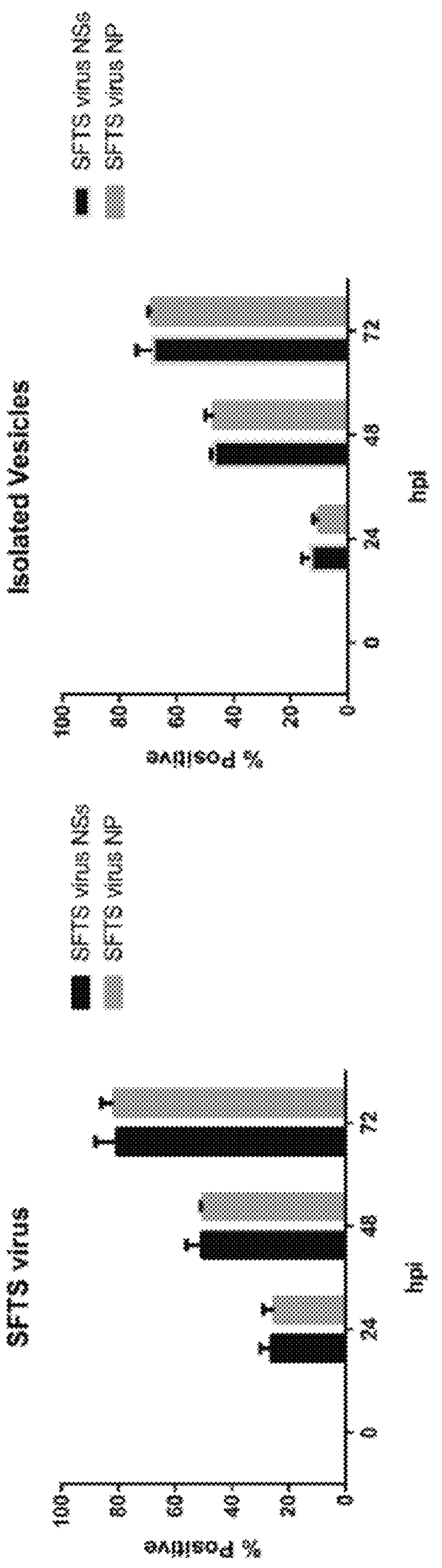

Extracellular vesicles produced during SFTS virus infection mediate receptor-independent transmission of SFTS virus. It has been previously shown that hepatitis C virus (HCV) hijacks secreted vesicles for receptor independent transmission of viral RNA (32, 39). Furthermore, hepatitis A virus (HAV) is released cloaked in host membranes in a release mechanism resembling those of exosomes (40, 41). Additionally, coxsackievirus B3 (CVB3) has been shown to target secreted vesicles for virus dissemination (33). We therefore hypothesized that extracellular vesicles produced during SFTS virus infection may mediate transmission of SFTS virus between cells. Extracellular vesicles were purified, subjected to immune selection using anti-CD63 and anti-SFTS virus antibodies, and incubated with SFTS virus mouse hyperimmune ascitic fluid as indicated above. Purified vesicles were overlaid onto uninfected HeLa cells pretreated with 2 μg/ml of either mouse anti-CD63 (FIG. 7A), mouse IgG1 (FIG. 7B), or mouse anti-SFTS virus antibodies (FIG. 7C). As a control, PBS was used for the Naive group (FIG. 7D). Supernatants were collected at 0, 24, 48, and 72 hpi and virus titer assayed by plaque assay. Consistent with our hypothesis, the purified extracellular vesicles were able to mediate productive infection of SFTS virus with titers at 24 hpi of $1.5\times10^3$ PFU/ml (FIG. 7D) and $1.85\times10^3$ PFU/ml (FIG. 7B) in the PBS- and IgG-treated HeLa cells, respectively. Interestingly, when cells were treated with anti-SFTS virus antibodies, we observed up to 1,000-fold reduction in viral titers in the SFTS virus control group; however, there was minimal effect on viral titers mediated by the purified vesicles (FIG. 7C). In contrast, we observed a 10-fold reduction in virus titer in cells treated with anti-CD63 antibody that were infected with the purified vesicles but no effect on viral titers mediated by SFTS virus (FIG. 7A). These data suggest that the extracellular vesicles produced during SFTS virus infection can mediate receptor independent transmission of SFTS virus. Lastly, to further confirm that the SFTS virus particles produced as a result of the infection with the extracellular vesicles can mediate additional rounds of replication, supernatants collected from cells infected with the purified, CD63 immune-selected extracellular vesicles described in FIG. 7D were used to infect HeLa cells. At 0, 24, 48, and 72 hpi, immunofluorescence was performed in the infected cells using antibodies against SFTS virus NP and NSs. As predicted, we were able to detect SFTS virus proteins at 24 to 72 hpi (FIGS. 8A-8B). Altogether, our results suggest that SFTS virus hijacks the secretory multivesicular endosomal pathway to mediate receptor-independent transmission of the virus.

Discussion

SFTS is a newly emerging viral hemorrhagic fever that was first described in China and has now been recognized in Japan and South Korea (1, 2, 9-11). Although human cases caused by SFTS virus have only been reported in Asia, the recent emergence of another tick-borne phlebovirus, Heartland virus, a close relative of SFTS virus, responsible for serious and fatal cases in the United States (3, 42), and the recognition of another tick-borne phlebovirus with zoonotic potential in Australia (43), named Hunter Island Group virus, have only underscored the need to increase our knowledge of how these novel phleboviruses cause disease and establish infection.

Recent studies conducted by us and others have determined that this pathogen counteracts innate immune responses via mechanisms distinct from those described for other bunyaviruses. Unlike any other bunyavirus nonstructural protein NSs, the SFTS virus NSs interacts with and relocalizes multiple components of the IFN response into cytoplasmic structures (18, 19, 44, 45). With regard to SFTS virus replication, it has been recently shown that these cytoplasmic structures might also play a role in virus replication because double-stranded RNA and the viral proteins NP and L that are known to be involved in virus replication colocalize within these structures (17). These structures were also found to colocalize with lipid droplets. Moreover, inhibitors affecting the synthesis of fatty acids negatively impacted the formation of these cytoplasmic structures, as well as virus replication (17). In an attempt to identify the source of these structures, we found that they were most likely of endosomal origin because the early endosomal marker Rab5, but no markers associated with the Golgi apparatus colocalized with these cytoplasmic structures (18).

Although these initial investigations provided preliminary knowledge on the source of these structures, it was still unclear whether these structures containing viral RNA traffic within the cells to incorporate the glycoproteins to form infectious virions. Thus, in order to provide further insights into the intracellular trafficking of these structures, we initially conducted live cell imaging studies on cells expressing SFTS virus NSs fused to the mCherry protein. Surprisingly, these investigations revealed that a portion of the SFTS virus NSs-expressing cytoplasmic structures were released into the extracellular space and were taken up by neighboring cells. Subsequent studies carried out in SFTS virus-infected cells further confirmed that the SFTS virus NSs was incorporated in extracellular vesicles produced by these cells and they carried virions capable of sustaining transmission of the virus to neighboring cells. Furthermore, the extracellular vesicles produced from cells expressing the SFTS virus NSs were not cellular debris released from dying cells because live cell imaging studies clearly showed that these structures were released from cells that were still alive and without noticeable damage. Additionally, SFTS virus does not induce a cytopathic effect on infected cells and these extracellular vesicles were detected in significant amount only 3 days after infection.

The extracellular vesicles produced by SFTS virus NSs-expressing cells and SFTS virus-infected cells displayed markers characteristic of exosomes, such as being positive for the tetraspanin CD63, a widely used exosome marker (46). Interestingly, we also found that the extracellular vesicles preferentially contain LC3-I rather than LC3-II. The limited detection of LC3-II lipidated form, which is known to associate with membranes upon the induction of autophagy (47, 48) and during infection with several different viruses, including poliovirus, rhinovirus, enterovirus 71, CVB3, and foot-and-mouth disease virus, among others (49-51), suggests that these structures are not derived from the autophagy pathway. Further, the shedding mechanism is distinct from the previously described autophagosome-mediated exit without lysis (AWOL) model for poliovirus release and also differs from a similar model described recently for CVB3 (33, 52). Since the nonlipidated form of LC3 is preferentially incorporated into the extracellular vesicles secreted by SFTS virus-infected cells, it is likely that this represents another example of a role for LC3 that is unrelated to autophagy. It has been previously reported that the nonlipidated form of LC3, referred as LC3-I, is also associated with membranes of the endoplasmic reticulum-associated degradation (ERAD) tuning vesicles (or EDEMosomes) and recent studies have suggested that these structures may serve as scaffold for positive-strand RNA virus replication complexes (53, 54). In our attempts to determine the source of the cytoplasmic structures induced by SFTS virus, we previously explored the possibility that they might be derived from the ERAD tuning pathway; however, we did not find any evidence supporting this possibility (18). In contrast, our data suggest that these structures are derived from the multivesicular endosomal pathway and might be classified as exosomes. Thus, our studies suggest that the nonlipidated form of LC3 is incorporated into extracellular vesicles of endosomal origin and may facilitate replication of negative-strand RNA viruses (such as SFTS virus) as well.

It has been recently shown that HCV hijacks exosomes to incorporate infectious RNA into these structures that are then capable of mediating receptor-independent transmission of the virus (32, 39). Here, we describe another model for subversion of exosome-like structures to mediate receptor-independent transmission involving the novel bunyavirus SFTS virus. Similar to the CVB3, but in contrast to HCV, we were able to detect one to five virions harbored within the exosome-like structures that were capable of establishing productive infection of cells that received them. These findings are quite remarkable because there have not been prior reports describing the localization of bunyavirus or any other arthropod-borne viruses within extracellular vesicles to mediate receptor-independent transmission of the virus. Thus, our findings highlight an elegant strategy by which the recently recognized SFTS virus subverts exosome-like structures for virus dissemination. Our data also suggest that this mechanism of infection is likely beneficial for SFTS virus because it provides a degree of protection against neutralizing antibodies and therefore contributes to the immune evasion properties of the virus. Future studies are needed to define the role of these "infectious exosome-like structures" in expanding the tropism of the virus and their contribution to viral pathogenesis. Additional studies are also needed to define exactly how these structures deliver the virus and viral RNA into the cells and the fusion mechanisms that probably occur between the viral and cellular vesicles membranes for infection to occur. Furthermore, studies are needed to determine whether the infectious extracellular vesicles are also produced during infection of the arthropod host and whether they play a significant role during the transmission cycle involving host and vector.

CITATIONS

1. Yu et al., 2011. Fever with thrombocytopenia associated with a novel bunyavirus in China. N Engl J Med 364:1523-1532.
2. Liu et al., 2014. Severe fever with thrombocytopenia syndrome, an emerging tick-borne zoonosis. Lancet Infect Dis 14:763-772.
3. Muehlenbachs et al., 2014. Heartland virus-associated death in Tennessee. Clin Infect Dis 59:845-850.
4. Yun et al., 2014. Severe fever with thrombocytopenia syndrome virus in ticks collected from humans, South Korea, 2013. Emerg Infect Dis 20:1358-1361.
5. Ding et al., 2013. Epidemiologic features of severe fever with thrombocytopenia syndrome in China, 2011-2012. Clin Infect Dis 56:1682-1683.
6. Jiao et al., 2012. Preparation and evaluation of recombinant severe Fever with thrombocytopenia syndrome virus nucleocapsid protein for detection of total antibodies in human and animal sera by double-antigen sandwich enzyme-linked immunosorbent assay. J Clin Microbiol 50:372-377.
7. Bao et al., 2011. A family cluster of infections by a newly recognized bunyavirus in eastern China, 2007: further evidence of person-to-person transmission. Clin Infect Dis 53:1208-1214.
8. Liu et al., 2012. Person-to-person transmission of severe fever with thrombocytopenia syndrome virus. Vector Borne Zoonotic Dis 12:156-160.
9. Zhang et al., 2011. Hemorrhagic fever caused by a novel tick-borne Bunyavirus in Huaiyangshan, China. Zhonghua Liu Xing Bing Xue Za Zhi 32:209-220. (In Chinese.)
10. Chang and Woo, 2013. Severe Fever with thrombocytopenia syndrome: tick-mediated viral disease. J Korean Med Sci 28:795-796.
11. Kim et al., 2013. Severe fever with thrombocytopenia syndrome, South Korea, 2012. Emerg Infect Dis 19:1892-1894.
12. Guu et al., 2012. Bunyavirus: structure and replication. Adv Exp Med Biol 726:245-266.
13. Palacios et al., 2013. Characterization of the Uukuniemi virus group (*Phlebovirus*: Bunyaviridae): evidence for seven distinct species. J Virol 87:3187-3195.
14. Fontana et al., 2008. The unique architecture of Bunyamwera virus factories around the Golgi complex. Cell Microbiol 10:2012-2028.
15. Novoa et al., 2005. Key Golgi factors for structural and functional maturation of bunyamwera virus. J Virol 79:10852-10863.
16. Salanueva et al., 2003. Polymorphism and structural maturation of bunyamwera virus in Golgi and post-Golgi compartments. J Virol 77:1368-1381.
17. Wu et al., 2014. Roles of viroplasm-like structures formed by nonstructural protein NSs in infection with severe fever with thrombocytopenia syndrome virus. FASEB J 28:2504-2516.
18. Santiago et al., 2014. Hijacking of RIG-I signaling proteins into virus-induced cytoplasmic structures correlates with the inhibition of type I interferon responses. J Virol 88:4572-4585.
19. Ning et al., 2014. Viral suppression of innate immunity via spatial isolation of TBK1/IKKε from mitochondrial antiviral platform. J Mol Cell Biol 6:324-337.
20. Bridgen et al., 2001. Bunyamwera bunyavirus nonstructural protein NSs is a nonessential gene product that contributes to viral pathogenesis. Proc Natl Acad Sci USA 98:664-669.
21. Blakqori et al., 2007. La Crosse bunyavirus nonstructural protein NSs serves to suppress the type I interferon system of mammalian hosts. J Virol 81:4991-4999.
22. Elliott and Weber, 2009. Bunyaviruses and the type I interferon system. Viruses 1:1003-1021.
23. Lozach et al., 2010. Entry of bunyaviruses into mammalian cells. Cell Host Microbe 7:488-499.
24. Komatsu et al., 2005. Impairment of starvation-induced and constitutive autophagy in Atg7-deficient mice. J Cell Biol 169:425-434.
25. Brennan et al., 2015. Reverse genetics system for severe fever with thrombocytopenia syndrome virus. J Virol 89:3026-3037.
26. Raposo and Stoorvogel, 2013. Extracellular vesicles: exosomes, microvesicles, and friends. J Cell Biol 200:373-383.

27. Escola et al., 1998. Selective enrichment of tetraspan proteins on the internal vesicles of multivesicular endosomes and on exosomes secreted by human B-lymphocytes. J Biol Chem 273:20121-20127.
28. Lai et al., 2015. Microvesicles: ubiquitous contributors to infection and immunity. J Leukoc Biol 97:237-245.
29. Pan et al., 1985. Electron microscopic evidence for externalization of the transferrin receptor in vesicular form in sheep reticulocytes. J Cell Biol 101:942-948.
30. Harding et al., 1984. Endocytosis and intracellular processing of transferrin and colloidal gold-transferrin in rat reticulocytes: demonstration of a pathway for receptor shedding. Eur J Cell Biol 35:256-263.
31. Valadi et al., 2007. Exosome-mediated transfer of mRNAs and microRNAs is a novel mechanism of genetic exchange between cells. Nat Cell Biol 9:654-659.
32. Ramakrishnaiah et al., 2013. Exosome-mediated transmission of hepatitis C virus between human hepatoma Huh7.5 cells. Proc Natl Acad Sci USA 110:13109-13113.
33. Robinson et al., 2014. Coxsackievirus B exits the host cell in shed microvesicles displaying autophagosomal markers. PLoS Pathog 10:e1004045.
34. Kalamvoki et al., 2014. Cells infected with herpes simplex virus 1 export to uninfected cells exosomes containing STING, viral mRNAs, and microRNAs. Proc Natl Acad Sci USA 111:E4991-E4996.
35. Mack et al., 2000. Transfer of the chemokine receptor CCR5 between cells by membrane-derived microparticles: a mechanism for cellular human immunodeficiency virus 1 infection. Nat Med 6:769-775.
36. Raposo et al., 1996. B lymphocytes secrete antigen-presenting vesicles. J Exp Med 183:1161-1172.
37. Pegtel et al., 2010. Functional delivery of viral miRNAs via exosomes. Proc Natl Acad Sci USA 107:6328-6333.
38. Zhang et al., 2013. An emerging hemorrhagic fever in China caused by a novel bunyavirus SFTSV. Sci China Life Sci 56:697-700.
39. Bukong et al., 2014. Exosomes from hepatitis C infected patients transmit HCV infection and contain replication competent viral RNA in complex with Ago2-miR122-HSP90. PLoS Pathog 10:e1004424.
40. Colombo et al., 2014. Biogenesis, secretion, and intercellular interactions of exosomes and other extracellular vesicles. Annu Rev Cell Dev Biol 30:255-289.
41. Feng et al., 2013. A pathogenic picornavirus acquires an envelope by hijacking cellular membranes. Nature 496:367-371.
42. McMullan et al., 2012. A new phlebovirus associated with severe febrile illness in Missouri. N Engl J Med 367:834-841.
43. Wang et al., 2014. Novel phlebovirus with zoonotic potential isolated from ticks, Australia. Emerg Infect Dis 20:1040-1043.
44. Wu et al., 2014. Evasion of antiviral immunity through sequestering of TBK1/IKKε/IRF3 into viral inclusion bodies. J Virol 88:3067-3076.
45. Ning et al., 2015. Disruption of type I interferon signaling by the nonstructural protein of severe fever with thrombocytopenia syndrome virus via the hijacking of STAT2 and STAT1 into inclusion bodies. J Virol 89:4227-4236.
46. Natasha et al., 2014. Exosomes as immunotheranostic nanoparticles. Clin Ther 36:820-829.
47. Kabeya et al., 2000. LC3, a mammalian homologue of yeast Apg8p, is localized in autophagosome membranes after processing. EMBO J 19:5720-5728.
48. Ichimura et al., 2000. A ubiquitin-like system mediates protein lipidation. Nature 408:488-492.
49. O'Donnell et al., 2011. Foot-and-mouth disease virus utilizes an autophagic pathway during viral replication. Virology 410:142-150.
50. Huang et al., 2009. Enterovirus 71-induced autophagy detected in vitro and in vivo promotes viral replication. J Med Virol 81:1241-1252.
51. Klein and Jackson, 2011. Human rhinovirus 2 induces the autophagic pathway and replicates more efficiently in autophagic cells. J Virol 85:9651-9654.
52. Bird et al., 2014. Nonlytic viral spread enhanced by autophagy components. Proc Natl Acad Sci USA 111:13081-13086.
53. Reggiori et al., 2010. Coronaviruses hijack the LC3-I-positive EDEMosomes, ER-derived vesicles exporting short-lived ERAD regulators, for replication. Cell Host Microbe 7:500-508.
54. Reggiori et al., 2011. Unconventional use of LC3 by coronaviruses through the alleged subversion of the ERAD tuning pathway. Viruses 3:1610-1623.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method for making an exosome comprising incubating an engineered cell under conditions suitable for production of an extracellular exosome, wherein the engineered cell comprises an exogenous polynucleotide encoding a nonstructural (NSs) protein of a virus that is a member of the Order Bunyavirales, or an active fragment thereof, wherein the extracellular exosome comprises marker LC3.

2. The method of claim 1 further comprising isolating the extracellular exosome.

3. The method of claim 1 wherein the virus is a member of the genus *Phlebovirus*.

4. The method of claim 3 wherein the member of the genus *Phlebovirus* is Severe fever with thrombocytopenia syndrome (SFTS) virus.

5. The method of claim 1 wherein the NSs protein has at least 80% similarity with SEQ ID NO:1.

6. The method of claim 1 wherein the number of extracellular exosomes produced by the cell is increased by at least 10-fold compared to the same cell that does not comprise the exogenous polynucleotide.

7. The method of claim 1 further comprising a glycoprotein (Gn protein) of a virus that is a member of the Order Bunyavirales, or an active fragment thereof.

8. The method of claim 1 wherein the extracellular exosome does not comprise a Severe fever with thrombocytopenia syndrome (SFTS) virus.

9. The method of claim 1 wherein the extracellular exosome further comprises an agent.

10. The method of claim 1 wherein the agent comprises a polynucleotide.

11. The method of claim 10 wherein the polynucleotide comprises mRNA, tRNA, rRNA, siRNA, microRNA, noncoding RNA, coding RNA, or DNA.

12. The method of claim 7 wherein the Gn protein has at least 80% similarity with SEQ ID NO:2.

13. The method of claim 7 wherein the Gn protein comprises SEQ ID NO:2.

* * * * *

SEQUENCE LISTING

```
<160> NUMBER OF SEQ ID NOS: 2

<210> SEQ ID NO 1
<211> LENGTH: 293
<212> TYPE: PRT
<213> ORGANISM: Phlebovirus SFTS virus

<400> SEQUENCE: 1

Met Ser Leu Ser Lys Cys Ser Asn Val Asp Leu Lys Ser Val Ala Met
1               5                   10                  15

Asn Ala Asn Thr Val Arg Leu Glu Pro Ser Leu Gly Glu Tyr Pro Thr
            20                  25                  30

Leu Arg Arg Asp Leu Val Glu Cys Ser Cys Ser Val Leu Thr Leu Ser
        35                  40                  45

Met Val Lys Arg Met Gly Lys Met Thr Asn Thr Val Trp Leu Phe Gly
    50                  55                  60

Asn Pro Lys Asn Pro Leu His Gln Leu Glu Pro Gly Leu Glu Gln Leu
65                  70                  75                  80

Leu Asp Met Tyr Tyr Lys Asp Met Arg Cys Tyr Ser Gln Arg Glu Leu
                85                  90                  95

Ser Ala Leu Arg Trp Pro Ser Gly Lys Pro Ser Val Trp Phe Leu Gln
            100                 105                 110

Ala Ala His Met Phe Phe Ser Ile Lys Asn Ser Trp Ala Met Glu Thr
        115                 120                 125

Gly Arg Glu Asn Trp Arg Gly Leu Phe His Arg Ile Thr Lys Gly Gln
    130                 135                 140

Lys Tyr Leu Phe Glu Gly Asp Met Ile Leu Asp Ser Leu Glu Ala Ile
145                 150                 155                 160

Glu Lys Arg Arg Leu Arg Leu Gly Leu Pro Glu Ile Leu Ile Thr Gly
                165                 170                 175

Leu Ser Pro Ile Leu Asp Val Ala Leu Leu Gln Ile Glu Ser Leu Ala
            180                 185                 190

Arg Leu Arg Gly Leu Ser Leu Asn His His Leu Phe Thr Ser Pro Ser
        195                 200                 205

Leu Arg Lys Pro Leu Leu Asp Cys Trp Asp Phe Phe Ile Pro Val Arg
    210                 215                 220

Lys Lys Lys Thr Asp Gly Ser Tyr Ser Val Leu Asp Glu Asp Asp Glu
225                 230                 235                 240

Pro Gly Val Leu His Gly Tyr Pro His Leu Met Ala His Tyr Leu Asn
                245                 250                 255

Arg Cys Pro Phe His Asn Leu Ile Arg Phe Asp Glu Glu Leu Arg Thr
            260                 265                 270

Ala Ala Leu Asn Thr Ile Trp Gly Arg Asp Trp Pro Ala Ile Gly Asp
        275                 280                 285

Leu Pro Lys Glu Val
    290


<210> SEQ ID NO 2
<211> LENGTH: 516
<212> TYPE: PRT
<213> ORGANISM: Phlebovirus SFTS virus

<400> SEQUENCE: 2

Asp Ser Gly Pro Ile Ile Cys Ala Gly Pro Ile His Ser Asn Lys Ser
1               5                   10                  15

Ala Gly Ile Pro His Leu Leu Gly Tyr Ser Glu Lys Ile Cys Gln Ile
```

-continued

```
            20                  25                  30

Asp Arg Leu Ile His Val Ser Ser Trp Leu Arg Asn His Ser Gln Phe
        35                  40                  45

Gln Gly Tyr Val Gly Gln Arg Gly Gly Arg Ser Gln Val Ser Tyr Tyr
    50                  55                  60

Pro Ala Glu Asn Ser Tyr Ser Arg Trp Ser Gly Leu Leu Ser Pro Cys
65                  70                  75                  80

Asp Ala Asp Trp Leu Gly Met Leu Val Val Lys Lys Ala Lys Glu Ser
                85                  90                  95

Asp Met Ile Val Pro Gly Pro Ser Tyr Lys Gly Lys Val Phe Phe Glu
            100                 105                 110

Arg Pro Thr Phe Asp Gly Tyr Val Gly Trp Gly Cys Gly Ser Gly Lys
        115                 120                 125

Ser Arg Thr Glu Ser Gly Glu Leu Cys Ser Ser Asp Ser Gly Thr Ser
    130                 135                 140

Ser Gly Leu Leu Pro Ser Asp Arg Val Leu Trp Ile Gly Asp Val Ala
145                 150                 155                 160

Cys Gln Pro Met Thr Pro Ile Pro Glu Glu Thr Phe Leu Glu Leu Lys
                165                 170                 175

Ser Phe Ser Gln Ser Glu Phe Pro Asp Ile Cys Lys Ile Asp Gly Ile
            180                 185                 190

Val Phe Asn Gln Cys Glu Gly Glu Ser Leu Pro Gln Pro Phe Asp Val
        195                 200                 205

Ala Trp Met Asp Val Gly His Ser His Lys Ile Ile Met Arg Glu His
    210                 215                 220

Lys Thr Lys Trp Val Gln Glu Ser Ser Ser Lys Asp Phe Val Cys Tyr
225                 230                 235                 240

Lys Glu Gly Thr Gly Pro Cys Ser Glu Ser Glu Glu Lys Ala Cys Lys
                245                 250                 255

Thr Ser Gly Ser Cys Arg Gly Asp Met Gln Phe Cys Lys Val Ala Gly
            260                 265                 270

Cys Glu His Gly Glu Glu Ala Ser Glu Ala Lys Cys Arg Cys Ser Leu
        275                 280                 285

Val His Lys Pro Gly Glu Val Val Val Ser Tyr Gly Gly Thr Arg Val
    290                 295                 300

Arg Pro Lys Cys Tyr Gly Phe Ser Arg Met Met Ala Thr Leu Glu Val
305                 310                 315                 320

Asn Pro Pro Glu Gln Arg Ile Gly Gln Cys Thr Gly Cys His Leu Glu
                325                 330                 335

Cys Ile Asn Gly Gly Val Arg Leu Ile Thr Leu Thr Ser Glu Leu Arg
            340                 345                 350

Ser Ala Thr Val Cys Ala Ser His Phe Cys Ser Ser Ala Ser Ser Gly
        355                 360                 365

Lys Lys Ser Thr Glu Ile His Phe His Ser Gly Ser Leu Val Gly Lys
    370                 375                 380

Thr Ala Ile His Val Lys Gly Ala Leu Val Asp Gly Thr Glu Phe Thr
385                 390                 395                 400

Phe Glu Gly Ser Cys Met Phe Pro Asp Gly Cys Asp Ala Val Asp Cys
                405                 410                 415

Thr Phe Cys Arg Glu Phe Leu Lys Asn Pro Gln Cys Tyr Pro Ala Lys
            420                 425                 430

Lys Trp Leu Phe Ile Ile Ile Val Ile Leu Leu Gly Tyr Ala Gly Leu
        435                 440                 445
```

-continued

```
Met Leu Leu Thr Asn Val Leu Lys Ala Ile Gly Val Trp Gly Ser Trp
    450                 455                 460

Val Ile Ala Pro Val Lys Leu Met Phe Ala Ile Ile Lys Lys Leu Met
465                 470                 475                 480

Arg Thr Val Ser Cys Leu Val Gly Lys Leu Met Asp Arg Gly Arg Gln
                485                 490                 495

Val Ile His Glu Glu Ile Gly Glu Asn Gly Glu Gly Asn Gln Asp Asp
            500                 505                 510

Val Arg Ile Glu
        515
```